(12) United States Patent
Golay et al.

(10) Patent No.: US 12,373,952 B2
(45) Date of Patent: Jul. 29, 2025

(54) METHOD FOR AUTOMATEDLY DISPLAYING AND ENHANCING AI DETECTED DENTAL CONDITIONS

(71) Applicants: Douglas A. Golay, Coon Rapids, IA (US); Wyatt C. Davis, Bozeman, MT (US)

(72) Inventors: Douglas A. Golay, Coon Rapids, IA (US); Wyatt C. Davis, Bozeman, MT (US)

( * ) Notice: Subject to any disclaimer, the term of this patent is extended or adjusted under 35 U.S.C. 154(b) by 176 days.

(21) Appl. No.: 18/089,443

(22) Filed: Dec. 27, 2022

(65) Prior Publication Data

US 2024/0212153 A1 Jun. 27, 2024

(51) Int. Cl.
*G06T 7/00* (2017.01)
*A61B 5/00* (2006.01)
(Continued)

(52) U.S. Cl.
CPC .......... *G06T 7/0016* (2013.01); *A61B 5/7425* (2013.01); *G06T 3/40* (2013.01); *G06T 7/11* (2017.01); *G06T 7/32* (2017.01); *G06T 2200/24* (2013.01); *G06T 2207/10116* (2013.01); *G06T 2207/20084* (2013.01);
(Continued)

(58) Field of Classification Search
CPC . G06T 7/0016; G06T 3/40; G06T 7/11; G06T 7/32; G06T 2200/24; G06T 2207/10116; G06T 2207/20084; G06T 2207/20092; G06T 2207/20224;
(Continued)

(56) References Cited

U.S. PATENT DOCUMENTS

| 2010/0121658 A1* | 5/2010 | Kaminski | A61C 19/00 715/790 |
| 2021/0073977 A1* | 3/2021 | Carter | G06T 11/20 |

(Continued)

*Primary Examiner* — Yujang Tswei

(57) ABSTRACT

A method for automatedly displaying and enhancing AI detected dental conditions which includes the steps of sending one or more images of dental information which is a 2d or 3d image or images containing dental anatomy to a convolution neural network-based machine learning software which has been trained to identify specific dental conditions or features, enacting of one or more machine learning convolution neural networks to detect a specific dental condition from a set of dental features or conditions, displaying one or more images with the detected dental conditions annotated graphically upon the image and in a location annotating the detected dental condition/feature, exposing in the user interface the ability for a user to select one of the possible many AI detections that are detected and annotated graphically upon the image, in response to user input, enacting an algorithm for the selected one of the possible many AI detections whereby said algorithm automates creation of multiple enhanced images using various combined proprietary image processing algorithms, applying various combinations of image processing algorithms to at a minimum the portion of the image which is defined via a region of interest and where the region of interest contains substantially all the features or dental conditions detected for the selected one of possible many AI detections selected within the image or images.

8 Claims, 20 Drawing Sheets

(51) Int. Cl.
*G06T 3/40* (2024.01)
*G06T 7/11* (2017.01)
*G06T 7/32* (2017.01)

(52) U.S. Cl.
CPC .............. *G06T 2207/20092* (2013.01); *G06T 2207/20224* (2013.01); *G06T 2207/30036* (2013.01)

(58) Field of Classification Search
CPC . G06T 2207/30036; G06T 2207/20081; A61B 5/7425
See application file for complete search history.

(56) References Cited

U.S. PATENT DOCUMENTS

| | | | |
|---|---|---|---|
| 2021/0074425 A1* | 3/2021 | Carter | G06N 20/00 |
| 2021/0192759 A1* | 6/2021 | Lang | A61B 34/20 |
| 2021/0377505 A1* | 12/2021 | Liu | H04N 13/246 |

* cited by examiner

METHOD FOR AUTOMATEDLY DISPLAYING AND ENHANCING AI DETECTED DENTAL CONDITIONS

BACKGROUND OF THE INVENTION

Field of the Invention

The present invention relates to image processing for analyzing and detecting features, i.e., dental pathologies, in (dental) radiographs, and, more particularly, to a system for analyzing radiographic image data from different imaging modalities by using machine learning methods to analyze and detect features, i.e., dental pathologies, in dental radiographs.

Description of the Prior Art

Digital imaging has notable advantages over traditional imaging, which processes an image of a physical object onto a physical medium. Digital imaging helps users such as health professionals avoid the costs of expensive processing equipment, physical paper, physical radiographs, and physical film. Techniques such as digital radiography expose patients to lower doses of radiation than traditional radiography and are often safer than their traditional counterparts are. Digital images are easy to store in storage such as a computer's hard drive or a flash memory card, are easy transferable, and are more portable than traditional physical images. Many digital imaging devices use sophisticated image manipulation techniques and filters that accurately image physical objects. A health professional's information infrastructures and business processes can therefore potentially benefit from digital imaging techniques. Though digital imaging has many advantages over physical imaging, digital imaging technologies are far from ubiquitous in health offices as existing digital imaging technologies present their own costs. To use existing digital imaging technologies, a user such as a health professional must purchase separate computer terminals and software licenses for each treatment room. As existing technologies install a full digital imaging package on each computer terminal, these technologies are often expensive and present users with more options than they are willing to pay for. Additionally, existing digital imaging technologies require users to purchase a complete network infrastructure to support separate medical imaging terminals. Users often face the prospects of ensuring software, which is installed at separate terminals maintains patient's confidentiality, accurately stores, and backs up data, accurately upgrades, and correctly performs maintenance tasks. As such, existing digital imaging technologies are not readily compatible with the objectives of end-users, such as health professionals.

In the fields of dentistry and other medical disciplines, flawed or inconsistent readings of x-ray images and other medical radiographs are relatively common. In the field of dentistry, an x-ray of a patient's teeth may be examined by a dentist for diagnosis or other purposes using the dentist's own judgment informed by experience and training. An individual dentist, doctor or other health provider may have limited experience with a particular diagnosis, anatomy, or anomaly, which may lead to inaccurate or missed diagnoses or treatment recommendations. Two health providers may have different opinions with respect to a diagnosis or treatment plan based on review of the same radiograph or set of radiographs captured for a particular patient. In the field of dentistry, dental practices often utilize existing computer software to manage, and review captured radiographs as digital image files. Some existing software or related computer tools further enable a dentist to review the digital files and manually mark (such as via user interface controls) features of interest that the dentist observes in each radiograph image.

Intraoral x-rays and extraoral x-rays have been used in dentistry to image teeth, jaw, and facial features for many years. In general, this process involves generating the x-rays from either an intraoral x-ray source or an extraoral x-ray source, directing the x-ray source at the patient's oral cavity and placing an image receptor device such as either a film or an electronic sensor to receive the x-rays from either the intraoral x-ray source or the extraoral x-ray source. The x-rays are attenuated by different amounts depending on the dental structure being x-rayed and whether it is bone or tissue. The resulting x-ray photons that pass through either the bone or tissue then form an image on the image receptor either the film or the electronic sensor. This image is then either developed (in the case of the film) or processed and displayed on a computer monitor in the case of the electronic sensor. Intraoral sensors are deployed to users by connecting the sensor to a PC or MAC which is in the dental office.

Local client/server software is installed on the client's PC. Images are saved to a server located in the dental practice. Likewise, extraoral sensors (panoramic/cephalometric) are also located in the dental office. Local client/server software is also installed on the client's personal computer (PC). The images are acquired by the local client server software and saved to a local server on a local area network. As software development methods and principles combined with new topology and deployment models have advanced, systems such as web (cloud) based imaging systems are desirable by users and vendors of dental imaging systems. These types of software applications employ software that is installed and deployed via a centrally located application server and maintained by professional IT personnel. The server is connected by a VPN/Internet connection to a remote location/office where clients who are running computers with a HTML web browser can display results of the imaging software located on the application server. It is minimal if any add-on or proprietary software is installed on the client in a cloud environment which reduces the customer requirement of having to install and maintain software or software upgrades. Additionally, because all images are maintained in cloud storage on the web, the images are automatically backed up and disaster recovery is available. And finally, the images in the cloud are available for viewing from any location which has any device that has a web browser unlike traditional client/server systems where the images are only readily available inside a local location/office and only when running proprietary locally installed client/server imaging software. Because all intraoral and extraoral x-ray imaging devices require drivers and/or some amount of proprietary software to operate, this limits the ability of the intraoral or extraoral 2D dental x-ray imaging devices to be able to communicate directly with an HTML web browser in the dental office environment for the purposes of acquisition of x-ray images or color images from a color intraoral camera or extraoral camera. To be able for HTML web browsers to acquire images or image data from a dental intraoral or extraoral sensor, extensions, or plug-ins (add on software) currently must be added to the web browser, which then allows communication with a dental imaging devices proprietary driver and/or application programming interface. These extensions (plug-in or controls) for the browsers are HTML web browser brand specific. Google Chrome browser cannot use the same plug-in that would be required for Microsoft Internet Explorer or for Apple Safari browser even when communicating with the same acquisition device. In addition, some browsers can run on different operating systems (Windows, Mac and IOS) and this most times requires the controls to be modified for each operating system as well. The above complexities make real cloud/web-based imaging not practical or adopted well for 2D dental intraoral and extraoral imaging device users who desire to acquire and display images via a standard HTML web browser without having to install traditional client server imaging software and/or without having to install, configure and maintain plug-ins for all browsers on all client devices that are desired to support acquisition from a dental imaging device. Indeed, today there exists only one publicly deployed dental cloud imaging application that supports acquisition to the cloud directly from an HTML web browser (Curve Dental/Curve Image) and it operates currently only upon one browser, on select operating systems, and with limited imaging sensor support because of the issues cited above when using a plug-in to control acquisition from a browser. It would be beneficial to allow a dental office to use any HTML web browser, on any operating system, and allow access to locally connected 2D dental imaging devices without adding any specific control, plug-in, or add-on to the web browser for the purpose to controlling or directing acquisition from these devices and accomplish the setup and installation of this capability automatically or semi-automatically. Dental radiographs are one diagnostic tool in dentistry. Dentists may have limited training in reading radiographs and little support from e.g., an additional radiological department, assisting them in their diagnosis. Due to such a large volume of radiograph data and limited analysis time, false negative and false positive errors may occur and could potentially lead to health risks and increased health costs due to missed detection or false treatment.

In the field of dentistry modern technologies of machine learning/artificial intelligence and sophisticated image processing algorithms are being applied to dental radiographic images and other dental 2D and 3D dental anatomy image data to assist the dentist with diagnosis of a dental condition, detection of dental conditions or features within a 2D or 3D image, and patient education. Many of these types of software-based products offer automated processing of a patient's dental images (typically x-ray images) to find dental conditions related to dental caries, 2D or 3D margins in teeth, radiolucency of periapical or other images, fractures, lesions, periodontal conditions, periodontal measurements, and detection of existing restorations in the dental anatomy image data including crowns, implants, and type/manufacturer of implant. Some of these software products overlay graphics or annotate directly upon the image to inform the user graphically via the user interface what dental conditions and/or dental features were detected within the 2D, or 3D image. These software's use various methods of overlaying labeling/annotating the AI detected condition upon the image; for example, a bounding rectangle box or circle around the detected condition area, a semi-translucent color covering the detected condition, or other graphical means to signify where that the AI had detected a dental condition/feature that the dentist should evaluate closer. Many of these software computer aided detection software products work well at quickly processing an image via AI/machine learning, typically using a CNN based method which has been trained to identify that specific dental condition or dental anatomy feature. Studies involving dental caries have shown that the AI/machine learning algorithms can typically perform more accurately and consistently versus human dentist interpretation.

U.S. Patent Application Publication No. 2021/0074425 teaches a system for automatically marking locations within a radiograph of one or more dental pathologies, anatomies, anomalies, or other conditions determined by automated image analysis of the radiograph by several different machine learning models. Image annotation data may be generated based at least in part on obtained results associated with output of the multiple machine learning models, where the image annotation data indicates at least one location in the radiograph and an associated dental pathology, restoration, anatomy, or anomaly detected at the at least one location by at least one of the machine learning models. Several different pathologies may be identified, and their locations marked within a single radiograph image.

U.S. Pat. No. 11,464,467 teaches a system for automated localization, enumeration, and diagnoses of a tooth/condition. The system detects a condition for at least one defined localized and enumerated tooth structure within a cropped image from a full mouth series based on any one of a pixel-level prediction, wherein said condition is detected by at least one of detecting or segmenting a condition on at least one of the enumerated tooth structures within the cropped image by a 2-D R-CNN.

U.S. Pat. No. 11,389,131 teaches a computer system which implements a neural network to process raw dental images to detect and number teeth and to diagnose pathological, non-pathological, and post-treatment conditions. Detected teeth, corresponding numbers, and any corresponding detected conditions are correlated to the dental image and presented in a graphical user interface comprising the image and a standard, symbolic dental chart associating the tooth number, detected conditions, and regions of the image to teeth represented in the symbolic chart.

U.S. Pat. No. 11,328,365 teaches a method for automatically identifying fraud, waste or abuse in health insurance claims submitted to insurance companies by healthcare providers. Insurance claim information and at one image associated with the insurance claim may be received, where the image has been submitted by a healthcare provider to an insurance carrier as supporting evidence of a medical service performed by the healthcare provider. The system may generate a digital signature representing the image, then may compare the digital signature generated for the image to previously generated digital signatures of other images that have been submitted in association with other insurance claims. The system may then determine the likelihood that the given insurance claim is associated with fraud, waste, or abuse, based in part on whether the digital signature is identical or close to one or more of the previously generated digital signatures.

U.S. Pat. No. 9,675,305 teaches a system for determining an orthodontic diagnostic analysis of a patient at various dental maturity stages which predicts future conditions and/or treatment recommendations. The system locates points in the mouth of a patient using an imaging device wherein the imaging device generates imaging data. The imaging data is transferred to a central processing unit wherein the central processing unit has access to a database having information associated with orthodontic conditions stored therein. The central processing unit obtains measurements associated with selected points and dentition in the mouth of the patient and predicts orthodontic conditions of the patient based upon the measurements and the information in the database. The central processing unit recommends treatments to the patient based upon the predicted orthodontic conditions.

U.S. Patent Application Publication No. 2022/0285026 teaches a method of making a diagnosis of a dental condition of a patient which includes the steps of collecting non-imaging data relating to the patient, storing the non-imaging data in a storage medium containing stored non-imaging data and existing imaging data for this patient and for a plurality of other patients and applying non-real time and non-user attended algorithms to the stored non-imaging data and the existing imaging data of this patient and other patients. The algorithms determine the diagnosis of the dental condition of the patient. The diagnosis either is complete or determines what new dental imaging data for the patient is required to be acquired to diagnose the dental condition of the patient. The non-imaging data includes non-clinical data and non-dental clinical data.

U.S. Patent Application Publication No. 2019/0313963 teaches a dental image feature detecting system which includes a computing device that includes a memory configured to store instructions. The system also includes a processor to execute the instructions to perform operations that include receiving data representing one or more images of dental information associated with a patient. Operations include adjusting the data representing the one or more images of dental information into a predefined format, wherein adjusting the data includes adjusting one or more visual parameters associated with the one or more images of dental information. Operations include using a machine learning system to determine a confidence score for one or more portions of the one or more images of dental information and producing a representation of the determined confidence scores to identify one or more detected features present in the one or more images of dental information.

The dental image feature detecting system can aid dental clinicians in their ability to interpret dental images, including but not limited to intra-extra oral radiographic imaging (e.g. bitewing and periapical radiographs), extra-oral radiographic imaging (e.g. panoramic x-ray), computed tomography scan (CT-scans) coming from a CT scanner, Positron emission tomography scan (PET-scans) coming from a Positron emission tomography-computed tomography scanner and Magnetic resonance imaging (MRI) scans coming from a MRI scanner, to correctly identify pathological lesions. By highlighting the potential features of interest, including but not limited to potential suspicious radiolucent lesions and potential carious lesions (also called cavities) and other pathological areas, the viewer of the radiograph can quickly recognize these detected features to reduce the number of missed lesions (false negatives) and wrongly identified lesions (false positives). By employing machine learning techniques and systems to analyze radiographs, which are presentable on displays, electronic or printed reports, etc., an evaluation of patient health condition can be efficiently provided, thereby allowing the dental professional to make an informed decision about treatment decisions. While many methodologies can be employed for pathology detection in dentistry, artificial intelligence techniques, such as deep learning algorithms, can exploit such radiographs, images information, for training and evaluation in an effective way. By developing such techniques, the diagnostic errors in dentistry can be reduced, pathologies can be detected earlier, and the health of the patients can be improved.

In the fields of dentistry and other medical disciplines, flawed or inconsistent readings of x-ray images and other medical radiographs are relatively common. In the field of dentistry, an x-ray of a patient's teeth may be examined by a dentist for diagnosis or other purposes using the dentist's own judgment informed by experience and training. An individual dentist, doctor or other health provider may have limited experience with a particular diagnosis, anatomy, or anomaly, which may lead to inaccurate or missed diagnoses or treatment recommendations. Two health providers may have different opinions with respect to a diagnosis or treatment plan based on review of the same radiograph or set of radiographs captured for a particular patient. In the field of dentistry, dental practices often utilize existing computer software to manage, and review captured radiographs as digital image files. Some existing software or related computer tools further enable a dentist to review the digital files and manually mark (such as via user interface controls) features of interest that the dentist observes in each radiograph image.

U.S. Patent Application Publication No. 2021/0073977 teaches a system for automated medical image annotating and presenting an interactive user interface that visually marks locations within a radiograph of one or more dental pathologies, anatomies, anomalies, or other conditions determined by automated image analysis of the radiograph by several different machine learning models. Annotation data generated by the machine learning models may be obtained, and one or more visual bounding shapes generated based on the annotation data. A user interface may present at least a portion of the radiograph's image data, along with display of the visual bounding shapes appearing to be overlaid over the at least a portion of the image data to visually mark the presence and location of a given pathology or other condition.

U.S. Pat. No. 10,878,954 teaches a system which provides artificial intelligence for automatic identification, localization, recognition, understanding, labelling, analyzing, assessing, deciding, and planning related to dento-craniofacial visual assets (herein referred as 'DCVA') for creating a report for patient treatment and consultation.

Starting the mid-nineties of the last century, a huge amount of dento-craniofacial visual assets has been continuously accumulating within many different repositories, ranging from universities, government agencies, insurance companies, research facilities, publishers, down to as small as polyclinics. Major World Wide Web search engines, like Google®, have also given access to a large amount of DCVA through their web search engines. One major problem facing the owners and users of these DCVA repositories is the complete absence of a system capable of parsing the many repositories, automatically recognizing the content, automatically building labels and metadata, and then optionally saving metadata in a query-ready computer formats to be used to respond to intelligent interrogations from all types of users. Another major problem is that all web search engines, like Google®, once applied to highly specialized data like DCVA fail badly by returning completely irrelevant images to the searched phrases. Proper DCVA search results are required for many aspects of dentistry, including providing information to insurance companies for pre-approval of expensive dental procedures. Dental Insurance treatment authorization for orthodontics cases is based on human inspection and evaluation of each DCVA individual case. This human dependent process is subjective and a slow and costly procedure, prone to human error and bias. Anonymization of patients DCVA to conform to privacy standards and legislations, for the large amount of digital assets, is a slow and costly procedure, but is required for research, analytics, business intelligence, machine learning and others.

Decomposing composite DCVA into labeled individual visual assets, as part of data preparation for any required procedure is also a slow and costly procedure. Selecting the proper individual visual assets and composing them in a new composite image (visual asset), conforming to standards, is a slow procedure. The multiple artificial intelligence systems and methods in the present system and method are aimed to solve all the foregoing problems.

U.S. Pat. No. 11,158,046 teaches a system for estimating measurements of craniofacial structures in dental radiographs and for receiving a dental radiographic image that includes an oral structure, and in an image processor, selecting a segmenter and an object detector, predicting masks and points of the oral structure using the segmenter and the object detector to become part of image metadata. The dental radiographic image and image metadata are further provided to a measurement processor for selecting at least one measurement method of a set of measurement methods according to the dental radiographic image and the image metadata, calculating a sensor pixel to mm (millimeter) ratio using the measurement method, and calculating a calibrated measurement of the oral structure.

U.S. Patent Application Publication No. 2022/0280104 teaches a method of making a diagnosis of a dental condition of a patient which includes the steps of collecting non-imaging data relating to the patient, storing the non-imaging data in a storage medium containing stored non-imaging data and existing imaging data for this patient and for a plurality of other patients and applying non-real time and non-user attended algorithms to the stored non-imaging data and the existing imaging data of this patient and other patients. The algorithms determine the diagnosis of the dental condition of the patient. The diagnosis either is complete or determines what new dental imaging data for the patient is required to be acquired to diagnose the dental condition of the patient. The non-imaging data includes non-clinical data and non-dental clinical data.

U.S. Patent Application Publication No. 2021/0353216 teaches a dental analysis system includes a computing device and a memory which is configured to store instructions. The dental analysis system also includes a processor to execute the instructions to perform operations that include receiving data representing one or more images of dental information which is associated with a patient. Operations include adjusting the data representing one or more images of dental information into a predefined format. Adjusting the data includes adjusting one or more visual parameters associated with the one or more images of dental information. Operations include using a machine learning system to determine a confidence score for one or more portions of the one or more images of dental information and producing a representation of the determined confidence scores to identify one or more detected features present in the one or more images of dental information.

Referring to FIG. 1 a dental analysis system 100, which U.S. Patent Application Publication No. 2021/0353216 teaches, includes an imaging machine, 102, e.g. an x-ray machine, which emits x-ray beams, 104, to an x-ray sensor, 106 (e.g., an intra-oral sensor, an extra-oral sensor, etc.) for taking radiographic images of the jaw and teeth of a patient. The x-ray sensor 106 is connected to a computing device (e.g., a computer system 108) including a display 110 capable of presenting radiograph information for review and study for the user of the dental analysis system, including but not limited to dental professionals (e.g. general dentists, endodontists, maxilla-facial surgeons), hygienists and other radiologists. One or more techniques, formats, etc. may be used to provide the radiographic data to the computer system 108; for example, the radiograph can be provided in a raw image data-format which will be processed by a sensor-specific software into digital imaging and communications in medicine (DICOM) or any other image format (tif, png, jpg etc.) by the computer system. The computer system 108 may also execute operations so one or more artificial intelligence techniques can be used to analyze this data and present results. In some environments, the computer system 108 can provide the data to other computing devices (e.g., a cloud computing system, service, etc.) to initiate a more distributed processing of the data. The machine learning techniques and other processes of the data utilize the dental image and associated dental image information, e.g., the age and gender of the subject, i.e. the patient, when the image was taken and other image meta-data such as x-ray sensor and model used, and other potential DICOM tags which do not constitute as personal health information. Once processed, analyzed data from the artificial intelligence techniques can be returned to the computer system for presentation and review (e.g., by a dental professional). The analyzed data of the dental image can be used in many ways: First, one or more presentation techniques may be employed by the computer system 108 to present the analyzed data; for example various types of user interfaces as one exemplified in interface 112 on the monitor 110, graphical representations, etc., may be used to efficiently present the data and quickly alert the professional to potential areas of interest signaling on the monitor 110 potential detected features which need immediate attention by the user. Detected features in the dental images may include radiolucent lesions, opaque lesions, other potential pathological lesions such as tooth-related radiolucent lesions, all types carious lesions, all kinds of periapical radiolucent lesions (including but not limited to cysts, infections etc.), bone fractures, tumors, osteonecrosis, other dental pathologies or obvious seemingly pathological radiolucent image parts and other features such as teeth and teeth-position/numbering, missing teeth, wisdom teeth, crowns, bridges, implants, and other anatomical characteristics such as bone density, height, width of the bones and angles, positioning, distances etc. between different facial structures (e.g. sinuses), tissues, gum and bone structures (e.g. implant and other treatment planning), margin tracing (e.g. if crowns are accurately placed on the tooth) and other assessments.

Second, the analyzed data, can provide an assessment of the dental image quality, e.g., create signals indicating that the dental image is not of high enough quality (e.g., blurry or the teeth structures are overlapping), and that an algorithmic analysis or a manual analysis by a user is not optimal, and can recommend taking another dental image. Third, the analyzed data can also be employed in a workflow such as being not visualized but instead (e.g., the area, the tooth number of the detected features, carious lesions on the dental image, etc.) can be compared to the diagnosis of the user as it is being input into, e.g., practice management software using, e.g., an API between the dental software system and such practice management software. If, the assessment of the user, e.g., location (tooth number and position) and/or type of detected feature, is not the same as the analyzed data, the dental analysis system can send one or more notifications to the user regarding the event.

By mapping the analyzed data to the associated data of the practice management system, the analyzed data can use time-series analysis and identify the progress (e.g., the health condition of a patient over period). Through such operations, the patient, user of the system, etc. are provided better information about potential diagnosis and treatment recommendations.

In one implementation, the dental analysis system cannot only be used prospectively but also retrospectively such as by analyzing retrospectively data, e.g., patient records of a dental practice and hospital and matching it with the analyzed diagnoses and treatment recommendations of the record, e.g., in the practice management system or the electronic health record, to estimate the quality of the dental practice and analyze if a potential recall of patients is necessary as dental features, e.g., carious lesions or other pathologies, have been missed.

The dental analysis system can also provide information such as transactional information to a payor, e.g., the health insurance, when submitting a claim. By algorithmically detecting features on the dental image and associated dental image information, the system may provide a probability factor that the diagnosis and recommended treatment of the dentist is accurate and thereby help the payor to detect distinct types of events (e.g., potential fraud) and conduct any additional analysis.

Upon one or more features being detected from a representation of the analyzed data, the detected features can assist in the execution of several functions such as 1) an assistive tool for the user, e.g., the dentist, to support his or her diagnosis and reduce false positive and false negative errors, 2) as a second opinion to a patient regarding their health conditions and to provide transparency to the diagnosis of the user, the dentist, the patient, etc. or 3) as an education tool for continuing education of dental professionals, dental students.

The imaging machine, 102, which emits x-ray beams, 104, to an x-ray sensor, 106 can be part of an intra-extra oral radiographic imaging machine (e.g. that produces bitewing and periapical radiographs), an extra-oral radiographic imaging machine (e.g. that produces panoramic x-ray), a dental cone beam computed tomography scan machine for CT-scans coming from a CT scanner (also called a CBCT-scanner), not radiology-emitting machines such as Positron emission tomography scan (PET-scans) coming from a Positron emission tomography-computed tomography scanner, Magnetic resonance imaging (MRI) scans coming from a MRI scanner.

Referring to FIG. 2 a computing environment 200 is presented that includes a computer system 202, that the user might interact with to view any software output on a display, 204. The software user-interface, 206, is presented (e.g., as requested by the user or automatically presented after a radiographic image is taken). The detected features are displayed using a colored bounding box 208 that surrounds the detected feature. In one arrangement of this user-interface, the colored box translates to a certainty score, which is decoded in colors, e.g., from green (low confidence) to red (high confidence), that the detected feature is indeed a detected feature. In an arrangement, functionalities of this software interface, 206, include user selectable icons 210 for executing various function such as deleting and adding detected features. The user can either add the detected features to the radiograph in case the user suggests that the algorithm missed a detected feature, or he can delete the detected features of algorithm 208. In one implementation, computing environment 200 is a dental analysis system that a user can provide feedback about the detected features by either "agreeing", "disagreeing", "clinically validated", "clinically unvalidated". The input of the user can then be used for additional training data to further improve operations of the machine learning system. After carefully reviewing the radiograph using e.g., functionalities such as contrast change, hiding the algorithmic suggestions and inversion 212, the user can generate a report 214 that automatically summaries the algorithmic findings, answers generic questions to what the detected features mean for the health of the patient, what treatment recommendations usually are given and gives the user an way to communicate to the receiver, e.g., patient or other types of information, recommendation for his review. The report, 216, can be printed, sent via email, or transferred by employing one or more other techniques in any other way to the receiver as provided by selectable icons 218. Another selectable button, 220, allows the receiver to easily communicate with the user (e.g., to schedule a follow-up appointment for further treatment or diagnosis, ask questions, etc.). This feature should allow the patient to not miss any important diagnostics or treatment due to a lack of effective follow-up.

Referring to FIG. 3 a computer environment 300 can interact with a user for viewing detected features (e.g., by interacting with user-interface 206, shown in FIG. 2). Once a dental image is taken through sensor 102 (shown in FIG. 1), the raw image data gets transferred to a computer system 302 included in environment 300. From there, either in the raw image data or the post-processed image data (e.g., after the sensor's manufacturer's proprietary algorithms have processed the raw image data), gets exported or otherwise transferred (e.g., being exported to a memory associated with an Image Retriever 304 that is executed by the computer system 302. In one implementation, the image retriever 304 is a desktop client which de-identifies the dental image data by deleting or substituting with a non-identifiable replacement all personal health information, e.g., name, date of birth etc. and retains as associated dental image information only HIPAA compliant data of the subject (e.g., patient), the image was taken such as the gender, age, x-ray manufacturer and model of the dental image. The image retriever 304 can check if a dental image is a valid image in terms of having a correct image format, is an image which can be processed by the algorithm, and other filtering rules can apply that the right meta-data etc. contained in the image. The image 306 together with its associated dental image information (e.g., age, gender, x-ray modality, sensor, model, other meta-data, etc.), gets transferred over one of more networks (e.g., the internet 308) to a feature detector 310. To provide the functionality of detecting features, the feature detector 310 may use various machine learning techniques such as deep learning techniques to improve the identification processes through training the system (e.g., expose multilayer neural networks to training data, feedback, etc.). Through such machine learning techniques, the feature detector 310 uses artificial intelligence to automatically learn and improve from experience without being explicitly programmed. Once trained (e.g., from x-ray images with and without identified detected features (also called annotations)), one or more images, representation of images, etc. can be input into the feature detector to yield an output. The machine learning may or may not be stored and retrieved at a storage device 316. In this example, access to an identifier 314 is provided through a computer system 312 (e.g., a server) located at the feature detector 310. Further, by returning information about the output (e.g., feedback), the machine learning technique being used by the identifier 314 can use the output as additional training information. Other training data can also be provided for further training. By using increased amounts of training data (e.g., dental images with and without detected features), feedback data (e.g., data representing user confirmation, correction, or addition of identified detected features), the accuracy of the system can be improved (e.g., to predict image features). The identifier 314 may assign a probability (e.g., numerical value ranging from 0 to 1, where a larger value is associated with greater confidence) that a pathology exists to each pixel in the dental image, which can be post-processed into various forms (e.g., see FIG. 1). An output is provided that represents a set of confidence scores for presence of detected image features (e.g., carious lesions and periapical lucencies), and a conditional probability map encoding the location of any detected image feature. In one arrangement, an augmented image 318 consisting of the original image, 306, the pixel-wise probability of a detected feature and a graphical representation, e.g., a bounding box, of the detected feature. This augmented image gets transferred back from the feature detector 310 to computer system 302 where the image or portion of the image can be either displayed in a regular dental image viewer, the user-interface 206, or other software user-interfaces. The entire dental image system, consisting of the retriever and the feature detector 310, can be either as described above both offline "on premise" on the computer system 302 and a connected network, such as the internet 308, or otherwise, completely offline on the computer system 302 or entirely in the cloud, meaning the internet 308.

Referring to FIG. 4 one or more techniques may be implemented to identify detected features in the dental images by executing operation on a computing device (e.g., the computing system 312). For such techniques, information may be used from one or more data sources. A large data set from many dental practices, hospitals or other institutions who obtain dental images, might be collected in a collected image database 404. The identifier 314 is executed by the computer system 312 (e.g., one or more servers), presents at the feature detector 310 (also shown in FIG. 3). In this exemplary arrangement, the identifier 314 includes an image collector 402, which is able to collect images from the collected image database 404 and the image information database 406 which has associated dental image information data stored such as age, gender, and other image information which may or may not be frequently accessed and used for the identifier 314, regulatory or computational reasons both of which are hosted in the storage device 316. In this arrangement, such image data may be collected by an image collector 402 and stored (e.g., in a collected image database 404) on a storage device 316 for later retrieval. In some arrangements, information associated with images, associated dental image information (e.g., pixel-wise information of the area of the detected features which was collected by using the annotator tool, information about the subject-a patient, the image was taken from, image attributes such as manufacturers, model, lighting time, etc.) may be provided and stored in an image information database 406. Retrieving the image data (stored in database 404) and/or image information (stored in the database 406), a machine learning trainer 408 is provided the data to train a machine learning inference 412 (Going forward, a "machine learning system" is defined to consist of both the machine learning trainer 408 and the machine learning inference 412). Various types of data may be used for training the system. Images (e.g., millions of images) can be used by trainer 408. Pristine images of dental images (e.g., portions of intra-oral bitewing or intra-oral periapical images), distorted images of dental images (e.g., synthetically altered versions), real-world images of dental intraoral cameras (e.g., images captured by individuals in real-world conditions that include one or more colored pictures of the teeth and gum inside the patient's mouth) may be used to train the machine learning inference 412. For some images of dental x-ray images (e.g., images of pristine full mouth series (i.e., a complete set of intraoral x-rays taken of a patients' teeth and adjacent hard tissue (often consisting of four bitewings, eight posterior periapicals, six anterior periapicals), synthetically altered versions of the same, etc.)), information that identifies each included dental image feature (e.g., labels) may be provided for training. Alternatively, for some images (e.g., captured under real-world conditions), identifying information (of included dental image features) may be absent. The trainer 408 can access the image collector data and use image collector data for training a machine learning model and store it at the output database 410. Once trained, the machine learning inference 412 may be provided with input data such as one or more images to identify the dental features to detect or if the image quality is too low is present in the images. After being trained using pristine, distorted, and real-world images of to be detected image features, images containing unidentified image features and captured under real-world conditions may be input for predicting the contained to be detected dental features (as illustrated in FIG. 2). The identifier 314 may output data that represents the predicted dental features or any other image features (e.g., too low of an image quality or the absence of such dental image features) determined through an analysis of the input image. Image information database 406 has corresponding information for the images in the collected image database 404 saved. This information includes, information of the subject (e.g., patient) from whom the x-ray was taken, e.g., age and gender of the individual, the imaging device information, e.g., the type of imaging device (x-ray, CT, etc.), the area/type of image (bitewing or periapical dental image), the hardware model and version and other settings of the imaging device when the image was taken (e.g. all standardized DICOM tags) and the annotations. The images from the collected image database can be presented to annotators (e.g., dentists, radiologists, other experts, or non-experts) to annotate or mark the region where a feature of interest (e.g., carious lesion which the identifier should be capable of identifying) is to be found. The annotator can mark these regions either using a drawing of a bounding box close around the feature of interest, by setting a point into the center of the feature of interest or by drawing an outline around the feature of interest. All these inputs are saved in the image information database 406 and can serve the trainer as training material. In one arrangement, each image does not only get an annotation from one individual but several individuals, e.g., three independent annotators, who annotate the same image. All annotations are typically saved in the image information database and a software module in the image collector 402 can automatically combine the multiple annotator annotations to generate a high-quality annotation. The multiple annotator annotations can be combined in a majority voting system (if the two annotators agree on an annotation, the annotations overlap with each other for at least 1 pixel or have a certain value of "Intersection over Union", or a weighted union of all annotation by weighting more to the intersected regions) to define a higher quality annotation (e.g. 2 of 3 annotators agree on an annotation, it can be considered to be very likely a correct annotation, meaning an actual feature of interest.). This system can be implemented in many ways such as having two annotators annotate images and add to data gathering system and then a third annotator serves as a referee and either agree or disagree with these annotations and improve the quality of the annotations. By improving the annotations in such a way, the machine learning trainer can gather a much higher quality of annotations. A single value can be output representing the existence or absence of a feature in the entire image. In other arrangements, however, the output may be a vector or a matrix, which include a considerable number of elements (e.g., 1,000,000 elements), one for each pixel, each carious lesion. A common output matrix can be a heatmap that has the same size as the input image (i.e., if image is in the size of 1440 by 1920 pixel, the matrix will have 1440 rows and 1920 columns) whose elements have a one-to-one correspondence to the pixels on the input dental image. Various types of data may be provided by each element to reflect how each individual pixel of input image is related to the to-be-detected feature, e.g., carious lesion (a cavity). Each element of the matrix may include a floating-point number that represents a level of confidence in detecting the feature, e.g., a carious lesion. In some arrangements, the sum of these element-wise quantities represent a predefined amount (e.g., a value of one) to assist comparing confidence levels and determining which dental image features, e.g., carious lesions, are closer matches. In this example, the output matrix (e.g., with 1440 by elements) from the machine learning inference 412 is stored in an output data database 410. A renderer 414 determines whether a detected image feature (e.g., carious lesion) are present based on the value of the confidence score and, for any lesion present, generates the coordinates of the lesion bounding box. The results determined by the renderer 414 (e.g., a list of pixel-coordinates of the detected feature and its rendered bounding box) can be stored on the storage device 316 (e.g., in an output data database 410) for later retrieval and use. The input images (captured under real-world conditions) and correspondingly identified be further used to train the machine learning trainer 408 or other artificial intelligence-based systems. The renderer 414 is using this heat map and creates an image containing the original radiograph with bounding boxes for any detected feature, the type of detected feature (e.g., carious lesion or periapical radiolucency), and a summary statement of the number and type of detected features, and a message stating that the image was analyzed by the software (with link to instructions/labeling). The renderer 414 can transfer the augmented image 318 (or initiate the transfer) either back to the local computer environment 302 or visualize the image over an internet-based software client.

U.S. Pat. No. 10,984,529 teaches a system for presenting an interactive user interface that visually marks locations within a radiograph of one or more dental pathologies, anatomies, anomalies, or other conditions determined by automated image analysis of the radiograph by several different machine learning models. Annotation data generated by the machine learning models may be obtained, and one or more visual bounding shapes generated based on the annotation data. A user interface may present at least a portion of the radiograph's image data, along with display of the visual bounding shapes appearing to be overlaid over the at least a portion of the image data to visually mark the presence and location of a given pathology or other condition.

Referring to FIG. 5A a networked computing environment 500, which U.S. Pat. No. 10,984,529 teaches a networked computing environment 500 which is suitable for implementing features of a medical image analysis system and associated client-side medical image viewer application.

The networked computing environment 500 includes network 508, a medical provider system 502, one or more image storage systems 503, and a medical image analysis system 520. To simplify discussion and not to limit the present disclosure, FIG. 5A illustrates only one medical provider system 502, though multiple medical provider systems may be present. The medical provider system 502 may be utilized by a specific dental practice or dentist, and several other dental practices or other healthcare providers may operate other medical provider systems that are in communication with the same medical image analysis system 520. The medical provider system 502 may be operated by a user within a variety of dental settings, such as primary care (family dental practice or internal medicine), emergency medicine, urgent care, and/or oral maxillofacial radiologists who review radiographs across these settings. The medical image viewer application 1204, may be installed on one or more computer systems within dental clinics, dental service organization offices, dental insurance providers and/or other settings. The medical image analysis system 120 can include API gateway 522, one or more data stores 524, an image conversion module 525, and machine learning components 530, which includes multiple pre-processing classifiers 532 and pathology detectors 534. While FIG. 5A specifically illustrates pathology detectors, the machine learning components 530 may additionally include various other detectors that are each trained to detect something other than a pathology, such as various anatomies, anomalies and/or restorations. As will be discussed below, the API gateway 522 can communicate with the medical provider system 502 and/or image storage system 503 (e.g., using a network 508, such as the Internet) to receive medical images, and coordinate subsequent image processing and analysis by the machine learning components 530. Although only one network 508 is illustrated, multiple distinct and/or distributed networks may exist. The various systems and other components illustrated in FIG. 5A, including interactions or communications between them, will be described in more detail below with respect to FIG. 5B.

Still referring to FIG. 5A the medical provider system 502 may include hardware and software components for establishing communications over a communication network 508. The medical provider system 502 may be equipped with networking equipment and network software applications (a web browser and/or a proprietary application associated with an operator of the medical image analysis system 520) that facilitates communications via one or more networks (for example, the Internet, an intranet, or a virtual private network). The medical provider system 502 may have varied local computing resources such as central processing units and architectures, memory, mass storage, graphics processing units, communication network availability and bandwidth, and so forth. The medical provider system 502 may include any type of computing system. The medical provider system 502 may include one or more desktop computers, laptop computers, and/or servers operated in association with a dental practice or other medical practice. The medical provider system 502 can include a data store 526. Data store 526 can be configured to store patient data, radiograph images, and/or other information used in a typical dental practice or other medical practice. The data store 526 may be local to the medical provider system 502 (such as physically located within a doctor's office, hospital, lab, or other medical facility), remote from the medical provider system 502, and/or distributed across multiple computing devices. Data store 526 may employ various security and privacy protocols known in the art for storage of medical data, including Health Insurance Portability and Accountability Act ("HIPAA") compliance. The data store 526 may be written to by a dental practice's existing third-party practice management and/or radiograph processing application(s) and may be monitored for new files by an image monitoring component 506 that is configured to operate in association with the medical image viewer application 504 and medical image analysis system 5120. The medical provider system 502 may include an image monitoring component 106 configured to monitor the data store 526 or other source of a dental practice's radiograph images for new images, as will be further discussed below. The image monitoring component 506 may be a stand-alone application or system extension, while it may be part of the medical image viewer application 504. The medical image viewer application 504 may be a computer program or application executed by the medical provider system 502 to provide various client-side functionality that will be described herein and may include an annotation display component 505 for generating and causing display of annotated radiograph images and associated user interfaces, as will be further described below.

Referring to FIG. 5B data flow 501 within the networked computing environment of FIG. 5A. For ease of illustration, the data flow of FIG. 5B does not specify whether individual communications between illustrated components or systems are over a network or are local within a single computing system or device. Components or subsystems as part of a single computing system in FIG. 5A may instead be remotely located relative to each other. Similarly, other systems or components illustrated as in network communication with each other in FIG. 5A may be operated together on a single computing system or may be in direct local communication with each other rather than communicating over a network.

Referring to FIG. 6, several different pre-processing modules, machine learning models, and post-processing modules may be collectively implemented to detect different pathologies, anatomies, restorations and/or anomalies depicted in a radiograph. The API gateway 522 may be responsible for managing calls to various routines and models for generating metadata, such as image annotations and associated labels or classifications. The API gateway 522 makes sequential calls to several pre-processing modules which preprocess the image data, which are shown in FIG. 6 as preprocessing modules 601A, 601B through 601N. It will be appreciated that there may be many pre-processing modules which are not illustrated. At least some of the pre-processing modules may adjust certain global features in x-rays or other radiograph images by way of image processing. These routines may be configured to enhance and/or standardize the image data before it is processed by machine learning models. One such example of pre-processing is histogram equalization. The pre-processing modules may include, but are not limited to: (a) a module configured to determine if an image is "whitewashed" such that no image processing techniques (e.g. gamma correction) will sufficiently recover useful information for subsequent processing; (b) a module configured to detect the orientation of the image and adjust the orientation such that subsequent models or modules are only required to handle one orientation; (c) a machine learning model configured to detect teeth or another specific anatomical feature; and/or (d) a machine learning model configured to classify the type of image, such as from possible classifications of panoramic, bitewing, and periapical. After the pre-processing modules have processed a given image, the API gateway 522 makes parallel calls to several different machine learning models (such as machine learning models 610A, 611A, 630A, among others) that have been previously trained to localize and classify (or detect) specific pathologies, anatomies, restorations, and/or anomalies. In doing so, the API gateway may pass forward partial metadata generated from the preprocessing modules, such as preprocessing modules 601A, 601B and 601N. This metadata may then be used by the post-processing routines associated with specific machine learning models, such as post-processing modules 610B, 611B and 630B. As illustrated, each of the detectors 610, 611, 630 and others not illustrated may include both a machine learning model and an associated post-processing module that is specific to the given machine learning model. Each of the specific detectors and/or the associated machine learning model may include one of the following, though others may be implemented or some excluded in other embodiments: a model for detecting the presence of bone loss; a model for detecting the presence of faulty restorations (such as restorations which contain open margins, sub margins, or overhangs); a model for detecting caries; a model for detecting recurrent decay; a model for detecting widened periodontal ligaments; a model for detecting existing restorations (such as crowns, root canals, metal and non-metal fillings, bridges, or implants); a model for detecting potential pathologies (such as cysts, bone lesions, cancerous growths or malignancies); a model to detect calculus; a model to detect existing anatomy (such as sinuses, nerves, nasal canals, orbits, or zygomas); a model to detect teeth by number; a model to detect crowns and roots of teeth; a model to detect the size of the airway; a model to detect quantity and quality of dental implant site; a model to detect third molar impaction; a model to detect jaw fractures; a model to detect facial trauma; a model to detect arch forms of jaws; and/or a model to detect orthodontic cephalometric tracings. In some embodiments, a single model may be trained to identify a large set of the above or all the above, in addition to individual models that detect individual conditions above. Both a first model and a second model may each individually be configured to detect multiple pathologies that are the same between the two models, but the models may have been trained using different machine learning algorithms. Two models employing different machine learning algorithms may each be trained to classify image data as depicting any of the same list of pathologies (such as twenty different pathologies) but may output different classification results for the same input images based on differences in the respective model's training data and/or specific machine learning algorithm or structure used for the model. Two or more machine learning models may be trained to detect the same or overlapping sets of potential pathologies, the medical image analysis system 520 may be configured to apply a voting methodology or other resolution process to determine an ultimate classification result based on collective output of the models. It will be appreciated that many known methods of ensemble learning may be used in which multiple alternative models are trained to make similar classification predictions using different supervised and/or unsupervised machine learning techniques. Other models may be specific to individual pathologies (such as a model trained to detect only a single pathology as opposed to any of a set of pathology classes or labels). Training of the various machine learning models may include data collection by way of individual annotation and/or consensus-based annotation Consensus may be arrived at programmatically in some embodiments, such as based on a Jaccard index being determined to be at or above a given threshold between two individual annotations. Consensus annotation may additionally or alternatively come from annotators directly working together to jointly annotate radiographs together. Still referring to FIG. 6 each machine learning model (such as machine learning model 610A) is coupled with a model-specific post-processing module (such as post-processing module 610B). Post-processing modules may merge, edit, and/or augment the produced metadata based on algorithmically combining output from machine learning models. One such example is reducing false positives in anatomical regions in which the predicted property is known never to exist. The functionality implemented by a given post-processing module may vary based on what the associated machine learning model is designed to localize and classify. If machine learning model 611A is configured to classify caries (which can only exist on teeth), the combination of this caries detection model and a tooth detection pre-processing module may be used by the post-processing module 611B to confirm that the machine learning model 611A did not classify a region as caries if the region was not also classified as a tooth in pre-processing. Certain machine learning models or detectors may produce metadata that is used by a subsequent detector or machine learning model. Detector 611 may be a sub-detector of detector 610. Detector 610 may localize a region in the image which has been predicted to contain a specific pathology, anatomy, restoration and/or anomaly. Then, the detector 611 may take this metadata as input and restrict its processing to only those regions of interest to it. Detector 610 may predict the presence of caries. Detector 611 may crop only those regions containing caries (as predicted by detector 610), then the detector 611 may classify only those regions for the caries (e.g., into dentin, into enamel, or into pulp). There may be more than one sub-detector for a given detector. There may also be a sub-detector to classify detected caries regions into differing categories, such as gross, mesial, occlusal/incisal, distal, facial, lingual/palatal, incipient, or recurrent. Once all detectors have generated their respective metadata, the API gateway 522 may construct or generate a final output message or metadata set that is passed back as the final response back to a requester.

U.S. Pat. No. 10,673,922 teaches an HTML web browser-based imaging system which supports acquisition of 2D x-ray radiographs, and which includes either a 2D x-ray imaging device or a 2D color imaging device and a client device located in a dental office. Software operating upon the client device and a cloud server with dental imaging software installed and means to receive and store images or image data. The client device and the cloud server are connected either directly or indirectly via either an internet connection or a VPN connection. The client device has capability of the HTML web browser so that it does not require either an add-on extension or plug-in to control acquisition of images from a dental x-ray sensor. The software communicates with the dental x-ray sensor and receives image or image data from the dental x-ray sensor. The software receives directions to initiate acquisition and/or to receive image or image data via communication from the application server and/or from the HTML web browser.

Referring to FIG. 7 an illustrative user interface 700 presents a radiograph that has been annotated based on the results of automated image analysis, along with various user interface controls that enable a viewing user to modify the visual presentation. The user interface may be presented by the medical provider system 502 based on annotation data received from the medical image analysis system 520, such as via API gateway 522. A clinician using medical provider system 502 may have requested to access and view a certain patient's radiographs using the medical image viewer application 504. The medical image viewer application 504 may have requested annotation data from the API gateway in response to the clinician's view request or may have previously requested the annotation data from the API gateway (in which case the annotation data may be retrieved from a locally stored copy and/or from cloud storage or other remote storage when the clinician requests to view a particular radiograph). The detected conditions are displayed as overlay content (such as bounding regions 730, 732 and 734) over an original x-ray image, where each overlay indicates to the practitioner which regions contain which specific detected conditions. The clinician can toggle over the image (such as using a mouse or touchscreen) to select or highlight each specific condition for further review. User interface 700 includes filter options that enable the user to filter the available radiograph images by chart number by selecting filter option 708. The imagery and associated metadata may be grouped into charts, where a chart pertains to a series of medical images obtained from a single capture event (such as x-rays captured for a given patient in a single session). A list of available images within the currently selected chart (Chart 1) are shown, and the image currently being viewed is indicated by bolded text 710 (reading "x098424.jpg," which may be a filename of the image). Pathologies identified in the displayed image (based on the machine learning methods described herein) are listed on the right side of user interface 700. Several pathologies 720 are listed and selectable by the user, as well as several non-pathologic conditions 722. Bounding region 730 may correspond to the "Root Canal" condition 724 from non-pathologic list 722, while bounding regions 732 and 734 may correspond to specific detected caries from pathologies list 720. Additionally included in the user interface 700 are user interface controls that may be interacted with by the user to modify the display of the image and/or the associated overlay content. These user interface control elements include contrast control 712, zoom control 714 and confidence threshold control 718, each of which will be further described below. While these controls are shown as sliders other forms of controls may be presented (such as drop-down menus, dedicated zoom in and zoom out buttons, text fields for entering numeric values, and/or others). A clinician may have logged in to a user account associated with the medical image viewer application 504, and then may have entered or selected a customized patent identifier (such as a name or number) of a patient for whom the clinician is interested in viewing one or more annotated radiograph images. After viewing the list of available x-rays for that patient, the clinician has selected a specific x-ray image 710, which has caused update of the user interface to display the selected image along with the various annotation content and condition information determined by the machine learning analysis. Overlay bounding region 730 includes an overlaid textual label indicating the condition (in this instance "Root Canal"). Each displayed bounding region may include a displayed overlay text label indicating the name of the pathology, anatomy, restoration, or anomaly that has been detected by the machine learning models. Labels may only be displayed as overlay content within the image for one or more pathologies or other conditions selected by the user from the lists 720 or 724 (such as the user's selection of the Root Canal condition option 724 in user interface 700). The clinician or other user selecting, clicking on, or rolling over a condition from lists 720 or 722 may cause that pathology or non-pathologic condition to be highlighted in an overlaid bounding box or other bounding region on the image, such as bounding boxes 730, 732 and 734. Each bounding region's shape within the overlay content may be color coded to indicate the confidence that the medical image analysis system 520 assigned to its identification of the pathology or condition label. A green bounding box may indicate a high confidence score (falling above a first threshold), gold may indicate a medium confidence score (falling above a second threshold) and red may indicate a low confidence score (falling above a third threshold). Different shapes, line styles or other visual differences may be used to distinguish confidence scores instead of or in addition to color differences. The user may adjust confidence threshold control element 718 to either add or remove display of certain bounding regions and associated conditions based on their confidence score. At an extremely high setting, the confidence threshold may serve to minimize false alarms and maximize specificity and/or precision. At an exceptionally low setting, it may serve to minimize false negatives and maximize sensitivity and/or recall. Setting the confidence threshold control element to its absolute highest setting (such as a threshold of 500), may result in the user interface being updated to display no overlay metadata or bounding regions, such that the radiograph image is displayed without any overlay.

More specifically, a user adjusting the confidence threshold control element 718 (presented as a slider control) may change the bounding boxes displayed to display all bounding boxes associated with a pathology or other label having a machine learning confidence value at or above the threshold selected by the user via the control element 718 (set at a threshold of 40 out of 100 in the illustrated example). If a user set the confidence threshold higher, such as to 80, several bounding boxes currently displayed and that have confidence thresholds between 40 and 79 may be removed from the displayed bounding region overlays on the given image. As further shown in user interface 700, contrast control element 712 may enable the user to temporarily correct or adjust the display contrast of the image, such that aspects or anatomies appear brighter or better illuminated than in the original image. Overlays (including bounding region shapes and any associated text) may be preserved while contrast adjustment takes place. Zoom control 714 may enable the user to zoom in or out within the image, such as to inspect one or more specific regions of the image more closely. The overlays may also be preserved while zoom adjustment takes place. In other embodiments, a rotation tool (not illustrated) may additionally enable a user to rotate the displayed image, with the overlays also rotating and continuing to be displayed during image rotation. The user interface may further display a recommended treatment plan for one or more pathologies, which may be determined from a stored association between a specific annotation label and a recommended treatment.

Referring to FIG. 8 a dentist office 800 has a local client device 810, which U.S. Pat. No. 10,673,922 teaches, has ability to operate a standard HTML web browser which has not had a plug-in or extension added to support acquisition from dental imaging device 820. The local client device 810 also operates a local software service 830. The application server 850 includes image software and services and storage 860 and has means to automatically detect what intraoral or extraoral imaging device 820 is currently connected to client device 810 via communicating across internet/wan connection 840. When a user connects a dental imaging device 820 to client device 810, service automatically prepares the sensor to take an image. The user can then expose the dental imaging device 820 and the image or image data is automatically sent to cloud server 850 for permanent storage by cloud imaging software and services 860. Cloud software 860 then can notify a client device or devices; if any are currently connected, that an image is available. If client device 810 is not connected to cloud software 860 then the cloud software 860 can notify of image availability when a client device or specific user does connect. This workflow allows acquiring images or image data quickly and automatically without requiring any user input, device selection or modality selection.

U.S. Pat. No. 10,572,625 teaches a combination dental imaging system and dental practice management, and charting system which includes a dental imaging device, a dental practice management and charting system and a bi-directional communication interface which couples the dental imaging system to the dental practice management and charting system. The combination dental imaging system and dental practice management and charting system also includes a code generator, a translator, and a correlator. The code generator generates an ADA CDT code. The translator translates the ADA CDT code into at least one property required by the dental imaging system to acquire dental images of a specific image type, format, and quantity. The correlator correlates the dental images to be acquired by the dental imaging system to the ADA CDT code so that the dental images are acquired by having at least one property set.

Referring to FIG. 9 a combination dental imaging system and dental practice management, and charting system, which U.S. Pat. No. 10,572,625 teaches for use in a dentist office 900, includes a practice management and charting system 920, a dental imaging system 930, a LAN connection 940, a WAN connection 950 and a bi-directional communication interface 960. The practice management and charting system 900 includes at least client device 3210 which displays practice management and e-claims capabilities. The dental imaging system 930 includes at least one 3D dental imaging device 933 and/or at least one 2D dental imaging device 932 and at least one client device 931. The client device 931 can display images from the dental imaging system 930. Using the capabilities of the bi-directional communication interface 960 the practice management and charting system 900 can bi-directionally communicate with the dental imaging system 930 via LAN 940 or WAN 950.

Still referring to FIG. 9 the bi-directional communication interface 960 includes a code generator 961, a translator 962 and a correlator 963. The bi-directional communication system 960 couples the dental imaging system 3300 to the dental practice management and charting system 920. The code generator 961 is coupled to the dental imaging system 930 and generates an ADA CDT code. The translator 962 translates the ADA CDT code into at least one property required by the dental imaging system 930 to acquire dental images of a specific image type, format, and quantity. The correlator 963 correlates the images acquired by the dental imaging system 930 to the ADA CDT code. The images are acquired by having at least one property set.

U.S. Pat. No. 10,937,160 teaches a processing method for dental images with artificial intelligence for e-commerce. In one scenario, a processing device receives a dental image. The dental image is processed with a deep neural network and matched to anatomy and pathology datasets in real time. The matched and identified dental image is matched to a dental treatment recommendation dataset to further produce a real time dental product recommendation for a patient. One or more artificial intelligence entities may provide in real time dental treatment recommendations and/or real time dental product recommendations to a dental professional and/or an individual. The process may also produce a diagnostic treatment aid and/or a product recommendation such as an orthodontic aligner. Artificial intelligence dental datasets may be provided to dental professionals, health care professionals, individuals and e-commerce organizations that may buy, sell, exchange and/or transfer this information over a communication network such as the internet and/or a cell phone.

Referring to FIG. 10 a processing method for dental images, which U.S. Pat. No. 10,937,160 teaches, is shown as a conceptual diagram demonstrating the use of at least one of a machine learning, a deep learning to process at least one of a dental image 1002, a dental image landmark 1016 with a deep neural network 1012 to produce a real time correlation dataset 1037. The system may instruct an aggregate server 1014 to process an aggregator 1016 to utilize a computer vision component 1018 to process at least one of: a dental image 1002, a dental image landmark 1016 with at least one of: a supervised annotated dental anatomy landmark dataset 1003, an unsupervised annotated dental anatomy landmark dataset 1004 to produce at least one of: a first real time anatomy confidence score 1020, a second real time anatomy confidence score 1021, a multiple real time anatomy confidence score 1022 and provide to a real time dental image dataset 1030. The process may also process at least one of a dental image 1002, a dental image landmark 1016 with at least one of: a supervised annotated dental pathology landmark dataset, an unsupervised annotated dental pathology landmark dataset 1008 to produce at least one of: a first real time pathology confidence score 1023, a second real time pathology confidence score 1024, a multiple real time pathology confidence score 1025 and provide to a real time dental image dataset 1030. The real time dental image dataset 1030 may be processed with a deep neural network to at least one of a supervised annotated dental treatment recommendation dataset, an unsupervised annotated dental treatment recommendation dataset 1026 to produce at least one of: a first real time confidence score for a dental treatment recommendation 1028, a second real time confidence score for a dental treatment recommendation 1029, a multiple real time confidence score for a dental treatment recommendation 1031 and provide to a real time dental treatment recommendation dataset 1014. Wherein, a real time dental treatment recommendation dataset 1014 contains at least one of: a real time dental treatment recommendation, a real time dental treatment recommendation for no treatment. The real time dental image dataset 1030 and the real time dental treatment dataset 1014 may be processed with a deep neural network to at least one of a supervised annotated dental product recommendation dataset, an unsupervised annotated dental product recommendation dataset 1027 to produce at least one of: a first real time confidence score for a dental product recommendation 1033, a second real time confidence score for a dental product recommendation 1034, a multiple real time confidence score for a dental product recommendation 1035 and provide to a real time dental product recommendation dataset 1015. Wherein, a real time dental product recommendation dataset 1015 contains at least one of: a real time dental product recommendation, a real time dental product recommendation for no product. Correlate at least one of a dental image 1002, a dental image landmark 1016, a supervised annotated dental anatomy landmark dataset 1003, an unsupervised annotated dental anatomy landmark dataset 1004, a supervised annotated dental pathology landmark dataset 1007, a unsupervised annotated dental pathology landmark dataset 1008, a real time dental image dataset 1030, a supervised annotated dental treatment recommendation dataset 1018, an unsupervised annotated dental treatment recommendation dataset 1026, a real time dental treatment recommendation dataset 1014, a real time dental treatment recommendation, a real time dental treatment recommendation for no treatment, a supervised annotated dental product recommendation dataset 1017, an unsupervised annotated dental product recommendation dataset 1027, a real time dental product recommendation dataset 1015, a real time dental product recommendation, a real time dental product recommendation for no product with an individual information dataset 1036 and provide to a real time correlation dataset 1037. Wherein, an individual information dataset 1036 includes at least one of an age, a first name, a gender, a middle initial, a middle name, a last name, a sex, a date of birth, a zip code, an address, a geographic location, a cell phone number, a telephone number, a current medication, a previous medication, a social security number, a marital status, an insurance, an insurance identification number, an email address, internet protocol address, a change of insurance, an employer, a change of employment, a change of zip code, a change of the previous medication, a change of a marital status, a change of gender, a location, a chance of location, a biometric measurement, a biometric sensor measurement, a genetic dataset, an internet browsing history, a dataset. FIG. 10 shows at least one of a processing device, an aggregator is configured to execute an instruction in any order and the processing server is configured to omit an instruction in any order. An instruction may include one of a match, an identity, a score, a rule, a train, a process, an exchange, a transfer, a purchase, a sell, an analysis, and an order.

U.S. Pat. No. 10,496,723 teaches a media acquisition engine which includes an interface engine that receives a selection from a plug-in coupled to a media client engine where a client associated with the media client engine identified as subscribing to a cloud application imaging service. The media acquisition engine further comprises a media control engine that directs, in accordance with the selection, a physical device to image a physical object and produce a media item based on the image of the physical object, the physical device being coupled to a cloud client. The media acquisition engine also comprises a media reception engine that receives the media item from the physical device, and a translation engine that encodes the media item into a data structure compatible with the cloud application imaging service. The interface engine is configured to transfer the media item to the plug-in.

Referring to FIG. 11 a networking system 1100 for providing one or more application imaging services. The networking system 1100 includes, by way of example but not limitation, a desktop computer 1102, a laptop computer 1104, a server 1106, a network 1108, a server 1110, a server 1112, a tablet device 1114, and a private network group 1120. The private network group 1120 includes by way of example but not limitation a laptop computer 1122, a desktop computer 1124, a scanner 1126, a tablet device 1128, an access gateway 1132, a first physical device 1134, a second physical device 1136, and a third physical device 1138. The desktop computer 1102, the laptop computer 1104, the server 1106, the server 1110, the server 1112, and the tablet device 1114 are shown directly connected to the network 1108 but can be grouped in a manner like the private network group 1120 without departing from the scope and substance of the inventive concepts disclosed herein. The desktop computer 1102 can include a computer having a separate keyboard, monitor, and processing unit. The desktop computer 1102 can integrate one or more of the keyboards, the monitor, and the processing unit into a common physical module. The laptop computer 1104 can include a portable computer. The laptop 1104 can integrate the keyboard, monitor, and processing unit into one physical module. The laptop 1104 can also have a battery so that the laptop 1104 allows portable data processing and portable access to the network 1108. Tablet 1114 can include a portable device with a touch screen, a monitor, and a processing unit all integrated into one physical module.

Any or all the computers 1102, the laptop 1104, and the tablet device 1118 can include a computer system. A computer system will usually include a processor, memory, non-volatile storage, and an interface. Peripheral devices can also form a part of the computer system. A typical computer system will include at least a processor, memory, and a device (e.g., a bus) coupling the memory to the processor. The processor can include a general-purpose central processing unit (CPU), such as a microprocessor, or a special-purpose processor, such as a microcontroller. The memory can include random access memory (RAM), such as dynamic RAM (DRAM) and static RAM (SRAM). The memory can be local, remote, or distributed. The term "computer-readable storage medium" includes physical media, such as memory.

Referring to FIG. 12, a cloud-based client engine 1104 can include a media client engine 1202, a plug-in and interface layer 1204, a device layer 1224, and a device driver layer 1226. Any or all the elements of the cloud-based client engine 1104 can reside on a single client, such as the desktop computer 1224. The elements of the cloud-based client engine 1104 can also be distributed across multiple clients that are located within a single private networking group. For instance, the elements of the cloud-based client engine 1104 can be distributed across the laptop computer 1222, the desktop computer 1224, and the tablet device 1228, all within the private networking group 1220. The media client engine 1202 in the cloud-based client engine 1104 can lie in the web application layer of the cloud-based client engine 1104. The media client engine 1202 can execute portions of a web application such as user interface elements with which users such as health professionals see, use, and interact. In some embodiments, the media client engine 1202 can execute portions of code written in PHP and/or scripts such as JavaScript. The media client engine 1202 can also access portions of a Structured Query Language (SQL) such as a Postgre SQL database stored on one or more cloud servers. The media client engine 1202 includes application-level image filters and/or enhancements. The media client engine 1202 can therefore allow a user such as a health professional to adjust factors such as an image's contrast, gamma values, brightness, opacity, and noise. The application-level image filters can also employ custom algorithms and models that are specific to a particular sensor used to obtain an image. Thus, application-level image filters in the media client engine 1202 can include specific algorithms for x-ray sensors, thermal sensors, oral sensors, and other sensors. The filtering algorithms available to a specific user such as a specific health care professional can depend on the terms of his or her cloud application imaging service. A specific health care professional can choose to purchase only those application-level filters inside the media client engine 1202 that he or she finds the greatest application to his or her practice. The plug-in and interface layer 1204 includes a media acquisition plug-in 1206 and a media acquisition engine 1208. The media acquisition plug-in 1206 integrates into the media client engine 1202 while the media acquisition engine 1208 interfaces with lower-level engines, such as the engines inside the device layer 1224. The device layer 1224 interfaces with the plug-in and interface layer 1204 and abstracts the device driver layer 1226 to allow a user of the media client engine 1202 to manage physical devices without intimately knowing the device driver's inner workings or functionality. The device layer 1224 further incorporates device interface engine 1210, a first physical device interface 1212, a second physical device interface 1214, and a third physical device interface 1216. The device interface engine 1210 can expose an application-programming interface (API) to the plug-in and interface layer 1204. Various programming languages and/or platforms, such as the C++ language, can form the basis of the API in the device layer 1224 layer. The API can allow the plug-in and interface layer 1204 to communicate with individual device drivers. The device interface engine 1210 can create a common, generic class that serves as the foundation for specific hardware devices (such as the first physical device 1134, the second physical device 1236, and the third physical device 1238). The common, generic class created by the device interface engine 1210 provides a template that allows higher-level engines, such as engines operating at the plug-in and interface layer 1204 and/or the media client engine 1202, to initialize devices or get the data of devices. The device interface engine 1210 can also build functionality unique to each individual hardware device on top of the common, generic device foundation. That is, a specific device (such as one of the first physical device 1234, the second physical device 1236, and the third physical device 1238) corresponding to a particular manufacturer can require a unique sequence of numbers to initialize. The device interface engine 1210 can also therefore implement specific sequences for devices to initialize. Each device implementation communicates with the device drivers available on the user's system and implements the protocols specific to each device. Each device implementation can be packaged into one or more standalone libraries that can be loaded on demand by the device interface engine 1210 and thus made available to the user. The device interface engine 1210 can also provide a discovery mechanism that informs the plug-in and interface layer 1204 which drivers are installed on the user's system. Users, such as health professionals, would therefore be limited from selecting, on the media acquisition engine 1202, a sensor or a physical device to which he or she lacks access. The first physical device interface 1212, the second physical device interface 1214, and the third physical device interface 1216 translate the commands from the device interface engine 1210 to a data structure that is compatible with their respective device drivers. One or more of the first physical device interface 1212, the second physical device interface 1214, and the third physical device interface 1216 can implement engines and/or modules that translate commands on the level of the APIs in the device interface engine 1210 (e.g., C++ 14 APIs) to commands that comports with the level of the individual device drivers. The device driver layer 1226 includes a first physical device driver 1218, a second physical device driver 1220, and a third physical device driver 1222. The device drivers 1218, 1220, 1222 can be written in a variety of languages and can be targeted to specific platforms based on a hardware manufacturer's specifications. The device driver layer 1226 can support various commercially available device drivers. The plurality of physical devices can include one or more devices that include sensor-based imaging technologies. Sensor-based imaging technology can include an intraoral sensor, a digital radiography device, a thermal-based imaging technology, and/or a dental imaging technology, among other technologies.

The inventor hereby incorporates all the above-referenced patents and patent application publications into this specification.

SUMMARY OF THE INVENTION

The present invention relates generally to a method for automatedly displaying and enhancing AI detected dental conditions which includes the steps of sending one or more images of dental information which is a 2d or 3d image or images containing dental anatomy to a convolution neural network-based machine learning software which has been trained to identify specific dental conditions or features, enacting of one or more machine learning convolution neural networks to detect a specific dental condition from a set of dental features or conditions, displaying one or more images with the detected dental conditions annotated graphically upon the image and in a location annotating the detected dental condition/feature, exposing in the user interface the ability for a user to select one of the possible many AI detections that are detected and annotated graphically upon the image, in response to user input, enacting an algorithm for the selected one of the possible many AI detections whereby said algorithm automates creation of multiple enhanced images using various combined proprietary image processing algorithms, applying various combinations of image processing algorithms to at a minimum the portion of the image which is defined via a region of interest and where the region of interest contains substantially all the features or dental conditions detected for the selected one of possible many AI detections selected within the image or images.

In the first aspect of the present invention AI annotations detected and displayed (annotated upon the image) are processed via a dental CNN machine learning algorithm trained to detect multiple dental conditions in dental anatomy images in the method for automatedly displaying and enhancing AI detected dental conditions.

In the second aspect of the present invention the method for automatedly displaying and enhancing AI detected dental conditions which includes the step of displaying multiple images (sets of images) simultaneously in the user interface where the multiple images are enhanced versions of the image being displayed and are based upon the proprietary image processing algorithms.

In the third aspect of the present invention the method for automatedly displaying and enhancing AI detected dental conditions which includes the step of magnifying one or more the images (sets of images) being displayed and automatically adjusting the zoom factor upon display of the images to highly magnify the defined region of interest area that contains the graphically annotated selected one of possible many AI dental feature or condition detected.

In the fourth aspect of the present invention the method for automatedly displaying and enhancing AI detected dental conditions which includes the step of exposing in the user interface the ability for a user to select one of the many possible AI detections that are detected and annotated graphically upon the image.

In the fifth aspect of the present invention the method for automatedly displaying and enhancing AI detected dental conditions which includes the step of enacting an algorithm for the selected one of the possible many AI detections to automate creation of multiple enhanced images using various combined proprietary image processing algorithms.

In the sixth aspect of the present invention the method for automatedly displaying and enhancing AI detected dental conditions which includes the step of applying various combinations of image processing algorithms to a portion of the image which is defined in a region of interest and where the region of interest contains substantially all the feature or dental condition area detected within the image.

In the seventh aspect of the present invention the method for automatedly displaying and enhancing AI detected dental conditions which includes the step of selecting which various combinations of image processing to apply to an image or a region of interest within an image based at last partially upon the type of AI detection graphically annotated.

In the eighth aspect of the present invention the method for automatedly displaying and enhancing AI detected dental conditions which includes the step of using data within the specific region of interest to automatically calculate values for optimizing variable algorithm parameters, thresholds, and strength of the image processing being applied to the specific region of interest and where the variable values set are at least partially based upon the specific pixel intensity value, pixel size, or area containing the specific AI detected dental feature or dental condition.

In the ninth aspect of the present invention the method for automatedly displaying and enhancing AI detected dental conditions which includes the step of displaying multiple images (sets of images) simultaneously in the user interface where the multiple enhanced versions of the image being displayed is based upon the proprietary image processing algorithms.

In the tenth aspect of the present invention the method for automatedly displaying and enhancing AI detected dental conditions which includes the step of optionally showing the original non-enhanced image in the set of images displayed whereby if the algorithm, which varies for the specific type of detection being processed uses multiple images to create or more enhanced images for display, then the images are aligned via sub-segmentation of the specific feature of that specific image to correlate the image data and display of the dental condition/feature within the multiple images and/or to graphically show data differences between the two or more regions of interest that have overlap or do not overlap of the AI detected condition/feature, and magnifying one or more the images (sets of images) being displayed and automatically adjusting the zoom factor upon display of the images to highly magnify the defined region of interest area that contains the graphically annotated specific AI dental feature or detection.

Othwhich and many of the attendant advantages will be more readily appreciated as the same becomes better understood by reference to the following detailed description and considered in connection with the accompanying drawings in which like reference symbols designate like parts throughout the figures.

DESCRIPTION OF PREFERRED EMBODIMENT

Figure 1:
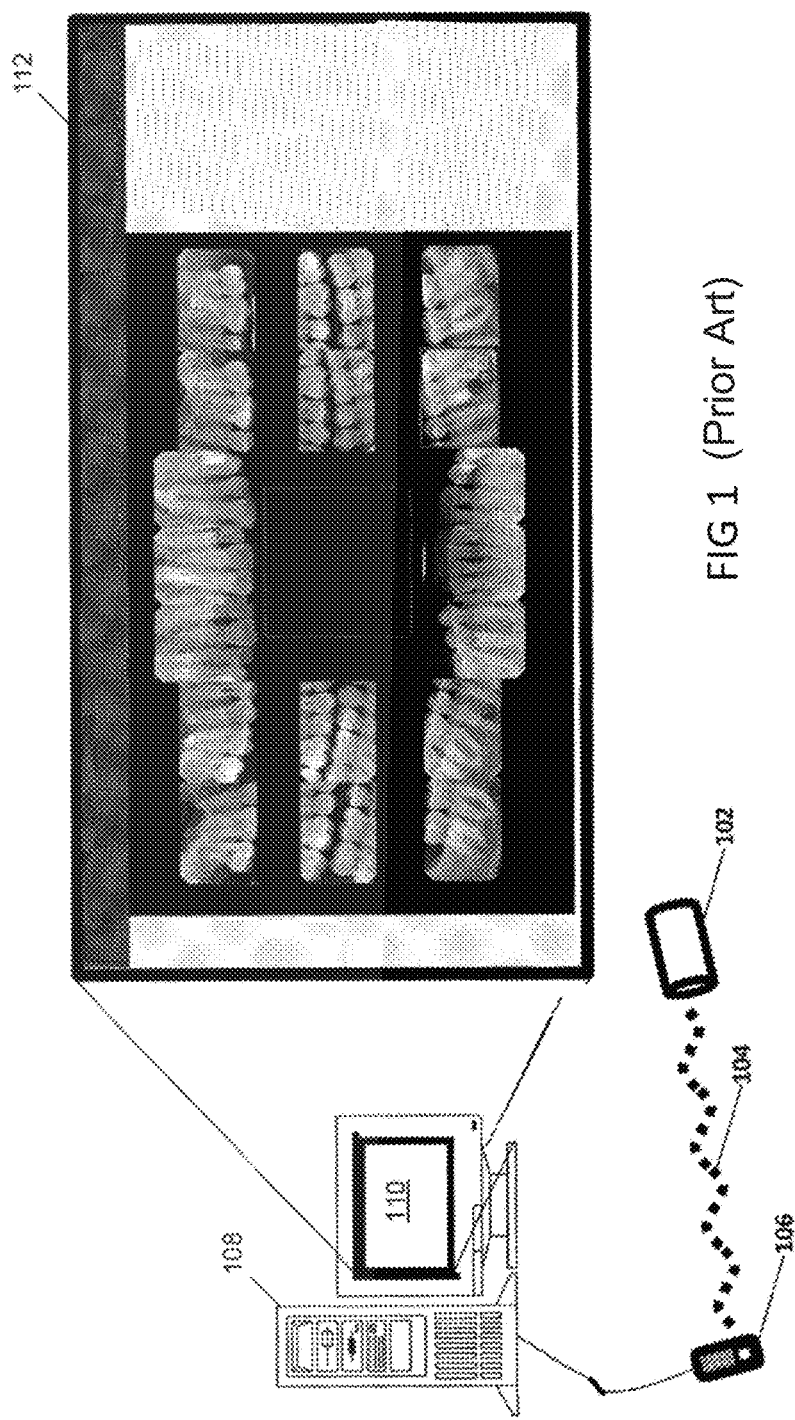
FIG. 1 is an illustration of a rated integration of software into a workstation of a dental professional according to U.S. Patent Application Publication No. 2021/0353216.
Figure 2:
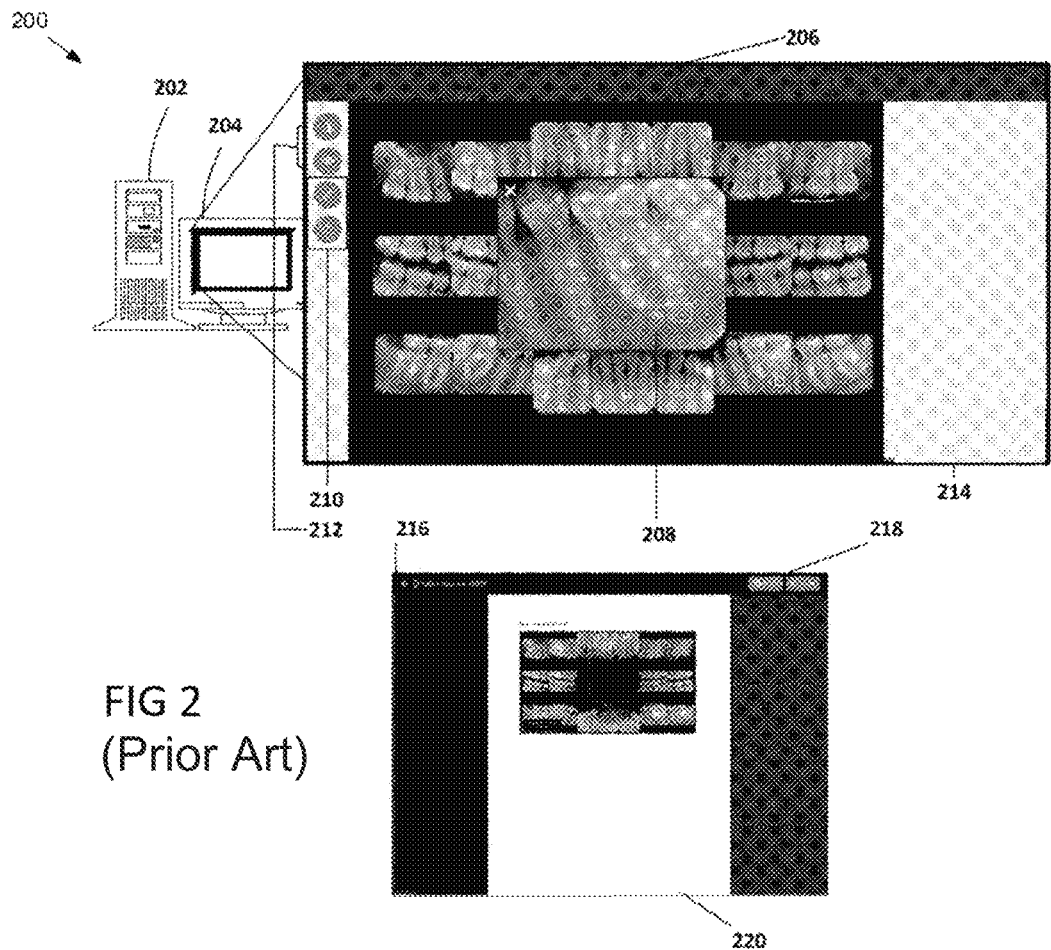
FIG. 2 is an illustration of functionalities of an artificial intelligence-based detection system according to U.S. Patent Application Publication No. 2021/0353216.
Figure 3:
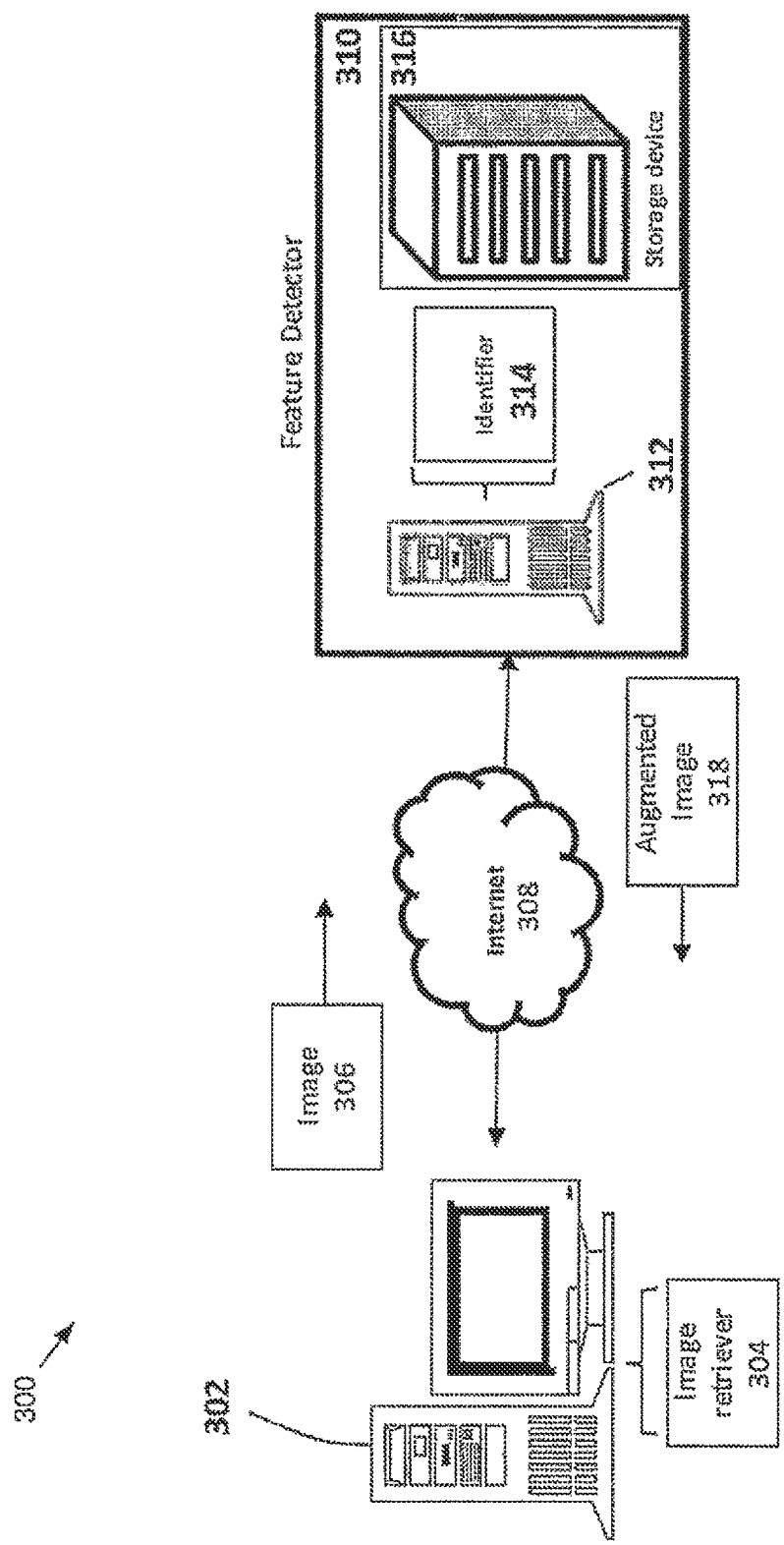
FIG. 3 is a block diagram of an internet-based computer network to provide detected features in dental imaging according to U.S. Patent Application Publication No. 2021/0353216.
Figure 4:
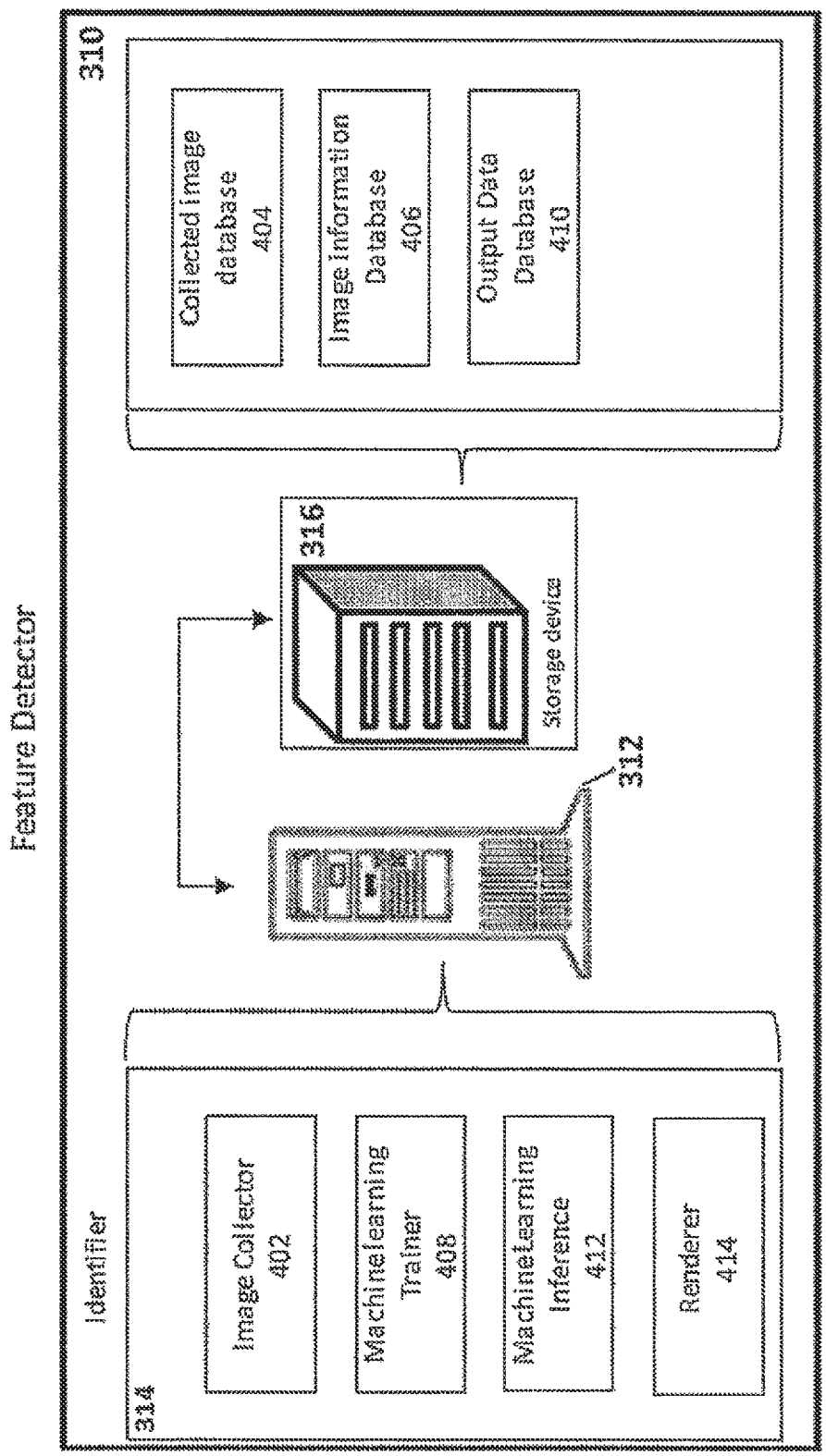
FIG. 4 a block diagram of a feature detector which manages and provides a detection of features in dental imaging according to U.S. Patent Application Publication No. 2021/0353216.
Figure 5A:
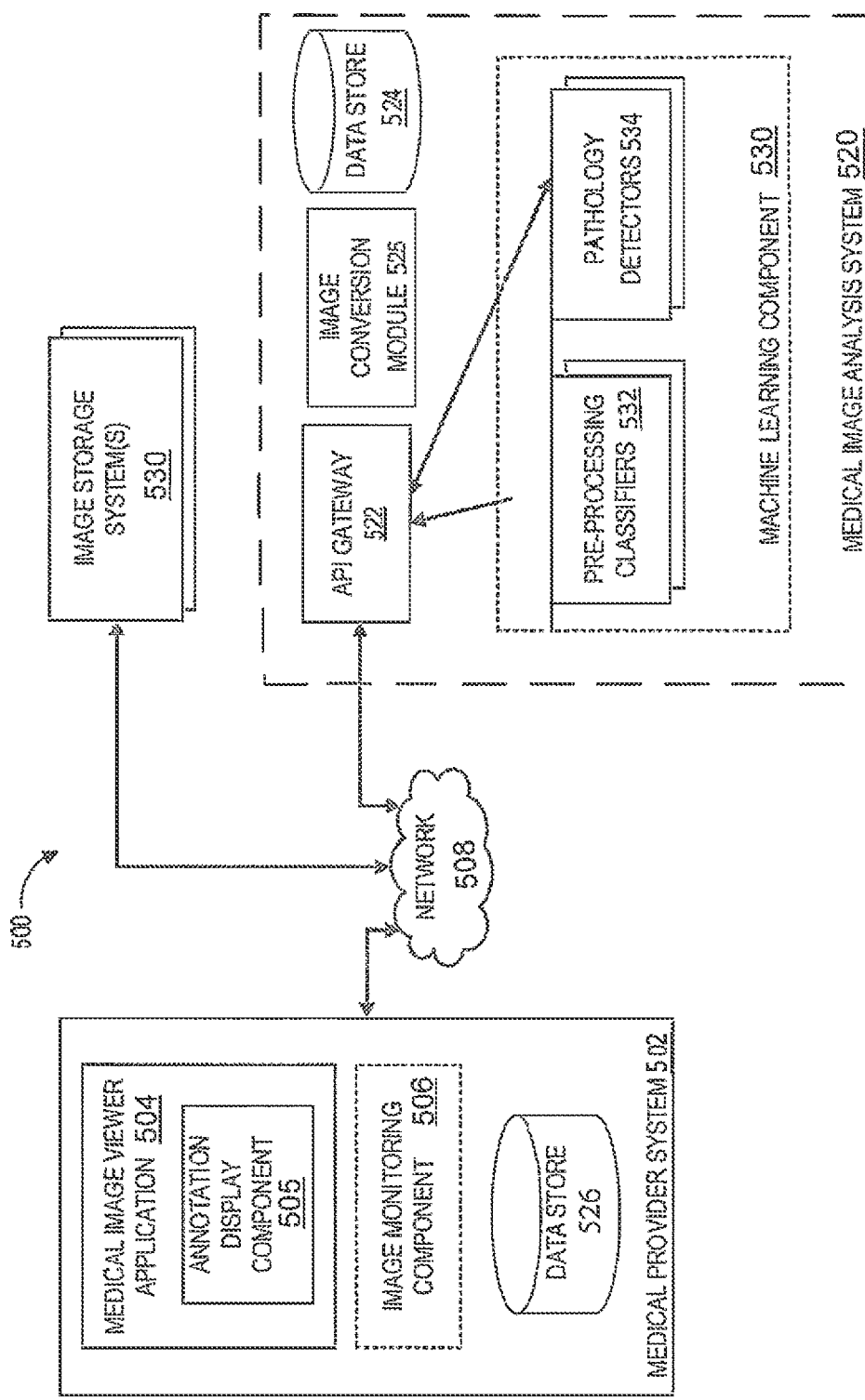
FIG. 5A is an illustration of a networked computing environment suitable for implementing features of a medical image analysis system and associated client-side medical image viewer application according to U.S. Pat. No. 10,984,529.
Figure 5B:
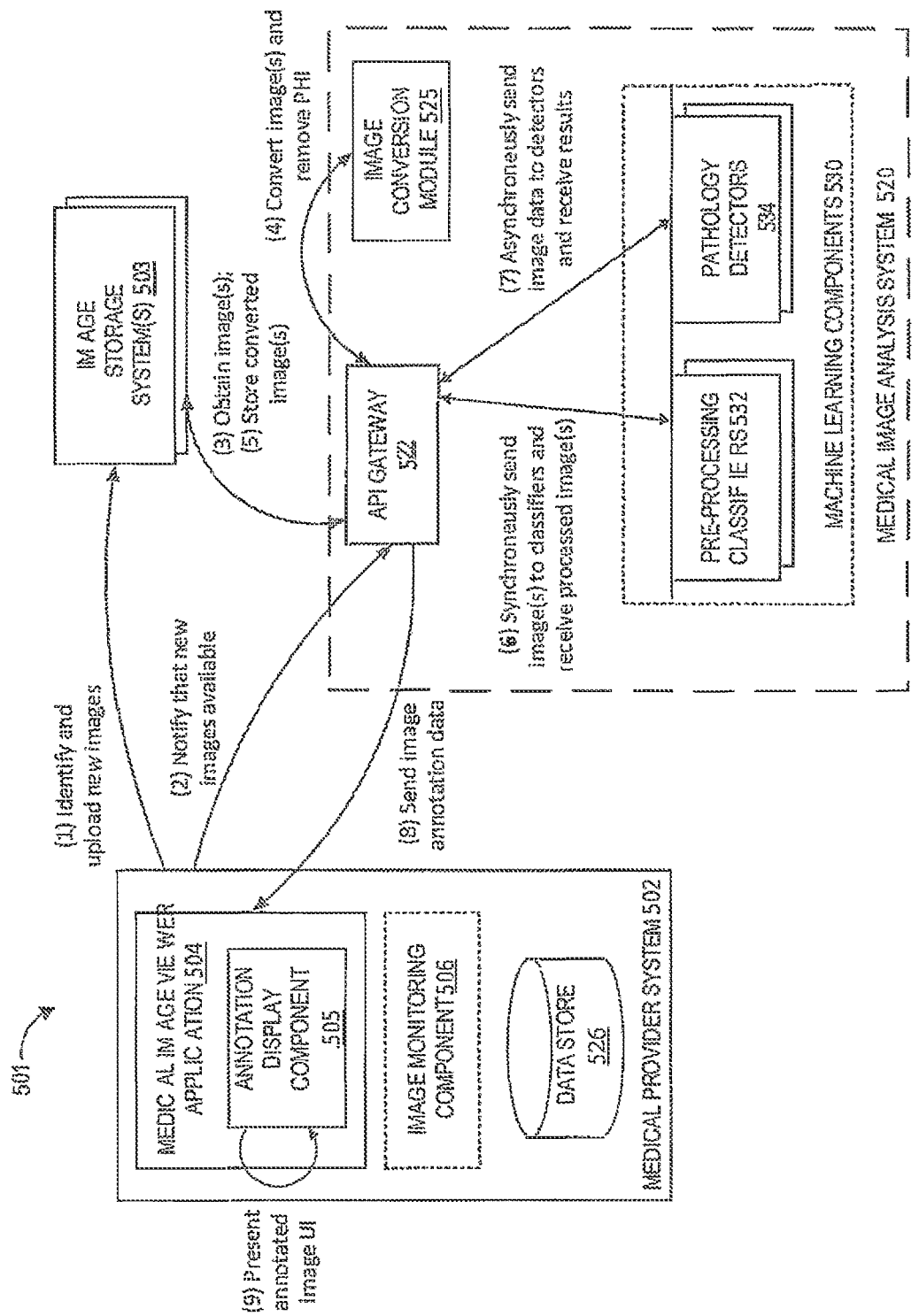
FIG. 5B is an illustration of data flow within the networked computing environment of FIG. 5A according to U.S. Pat. No. 10,984,529.
Figure 6:
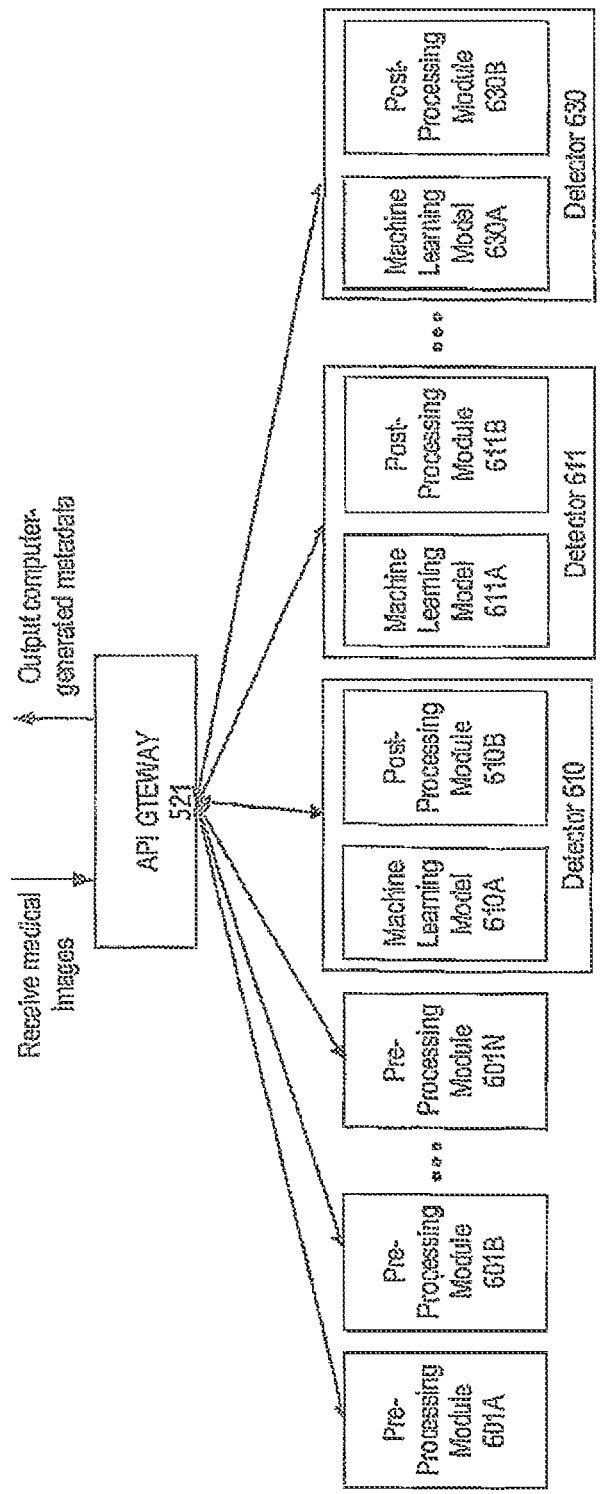
FIG. 6 is an illustration of several different pre-processing modules, machine learning models, and post-processing modules that may be collectively implemented to detect different pathologies, anatomies, restorations and/or anomalies depicted in a radiograph according to U.S. Pat. No. 10,984,529.
Figure 7:
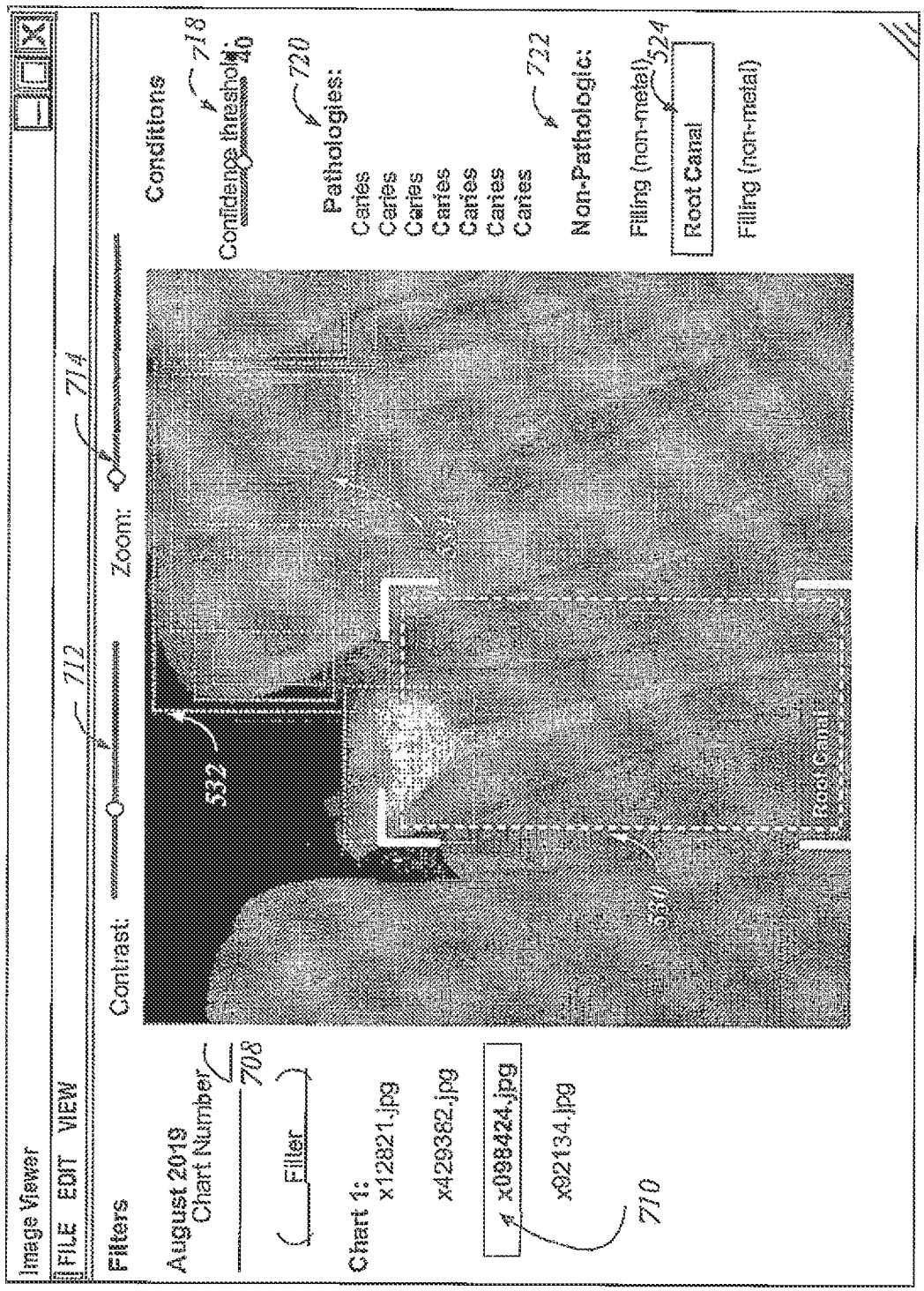
FIG. 7 is an illustration of a user interface that presents a radiograph that has been annotated based on the results of automated image analysis, along with various user interface controls that enable a viewing user to modify the visual presentation according to U.S. Pat. No. 10,984,529.
Figure 8:
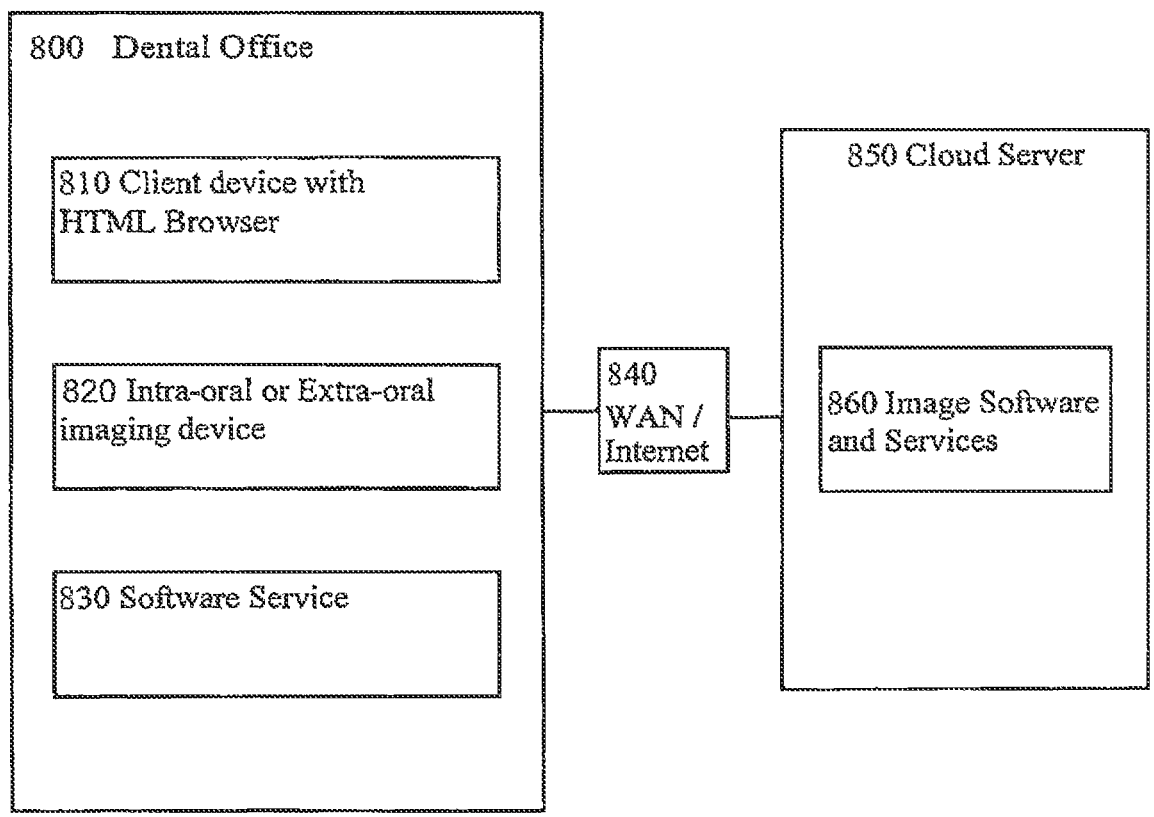
FIG. 8 is a schematic diagram of a dentist office with a wan/internet connection and a cloud server according to U.S. Pat. No. 10,673,922.
Figure 9:
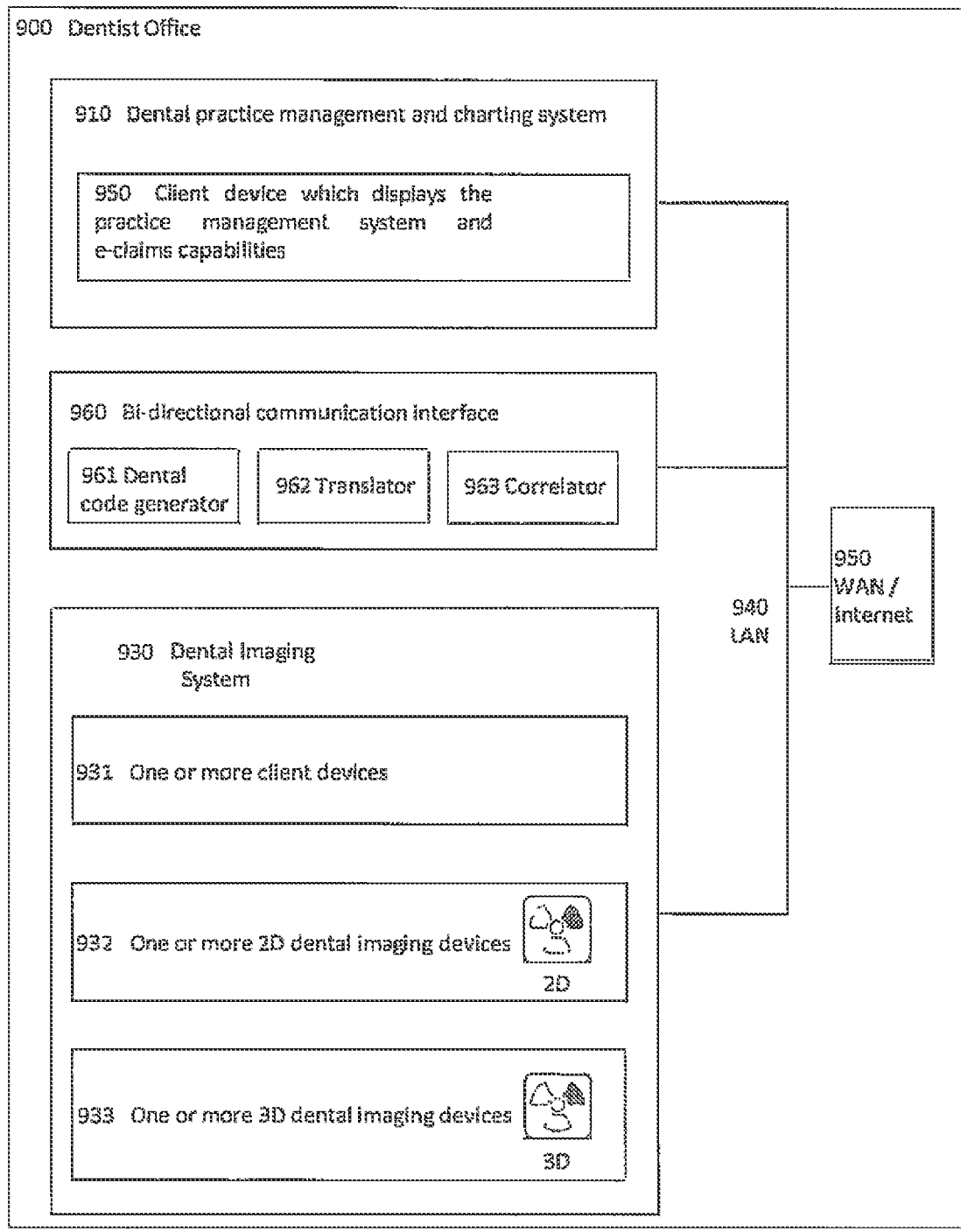
FIG. 9 is a diagrammatic drawing that includes dentist office, a practice management and charting system, a dental imaging system, a LAN connection, a WAN connection, a bi-directional communication interface, a code generator, a translator, and a correlator according to U.S. Pat. No. 10,572,625.
Figure 10:
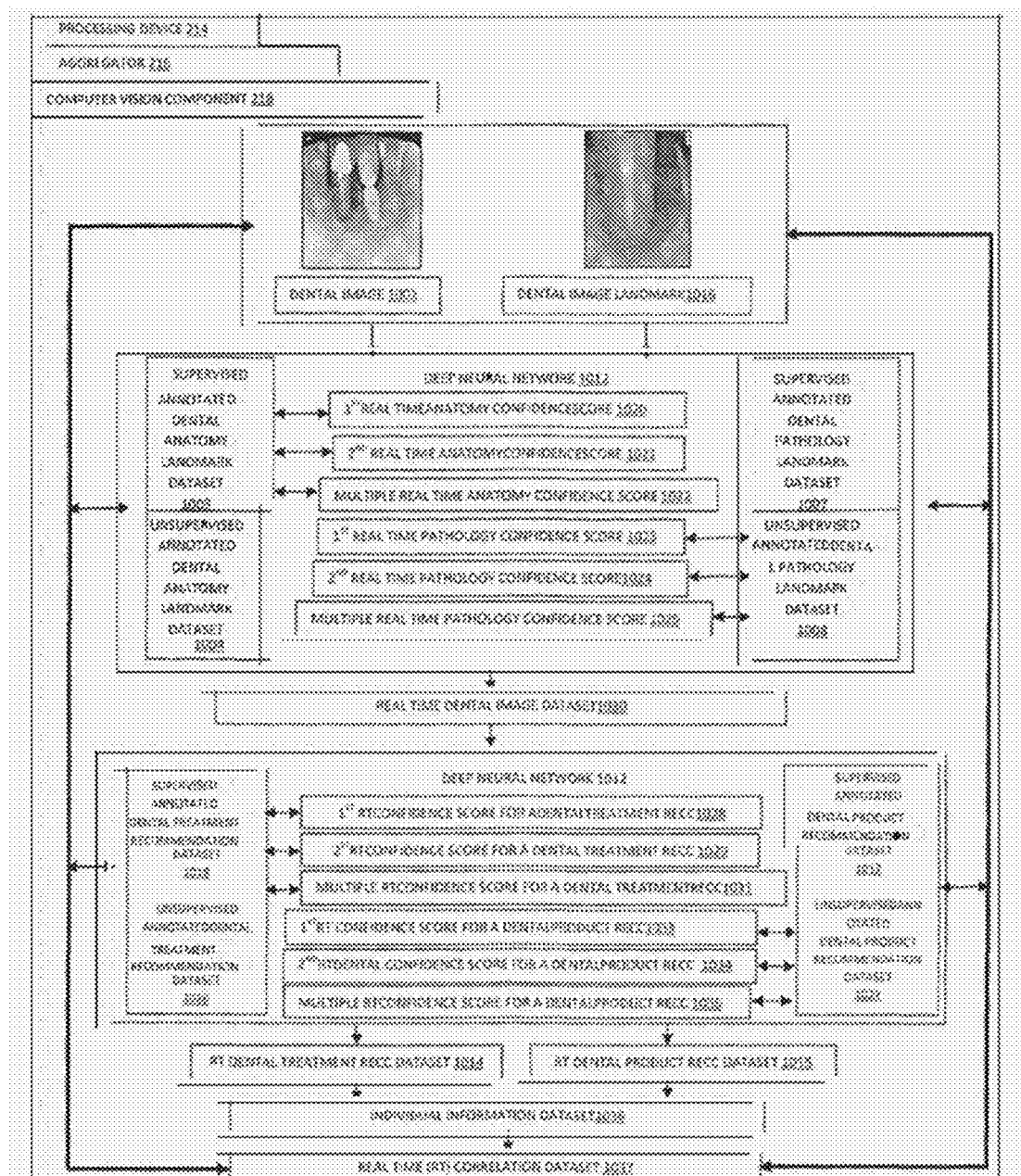
FIG. 10 is a conceptual diagram of a method for facilitating matching and identifying a dental image with a supervised and/or unsupervised annotated deep neural network to produce a real time correlation dataset according to U.S. Pat. No. 10,937,160.
Figure 11:
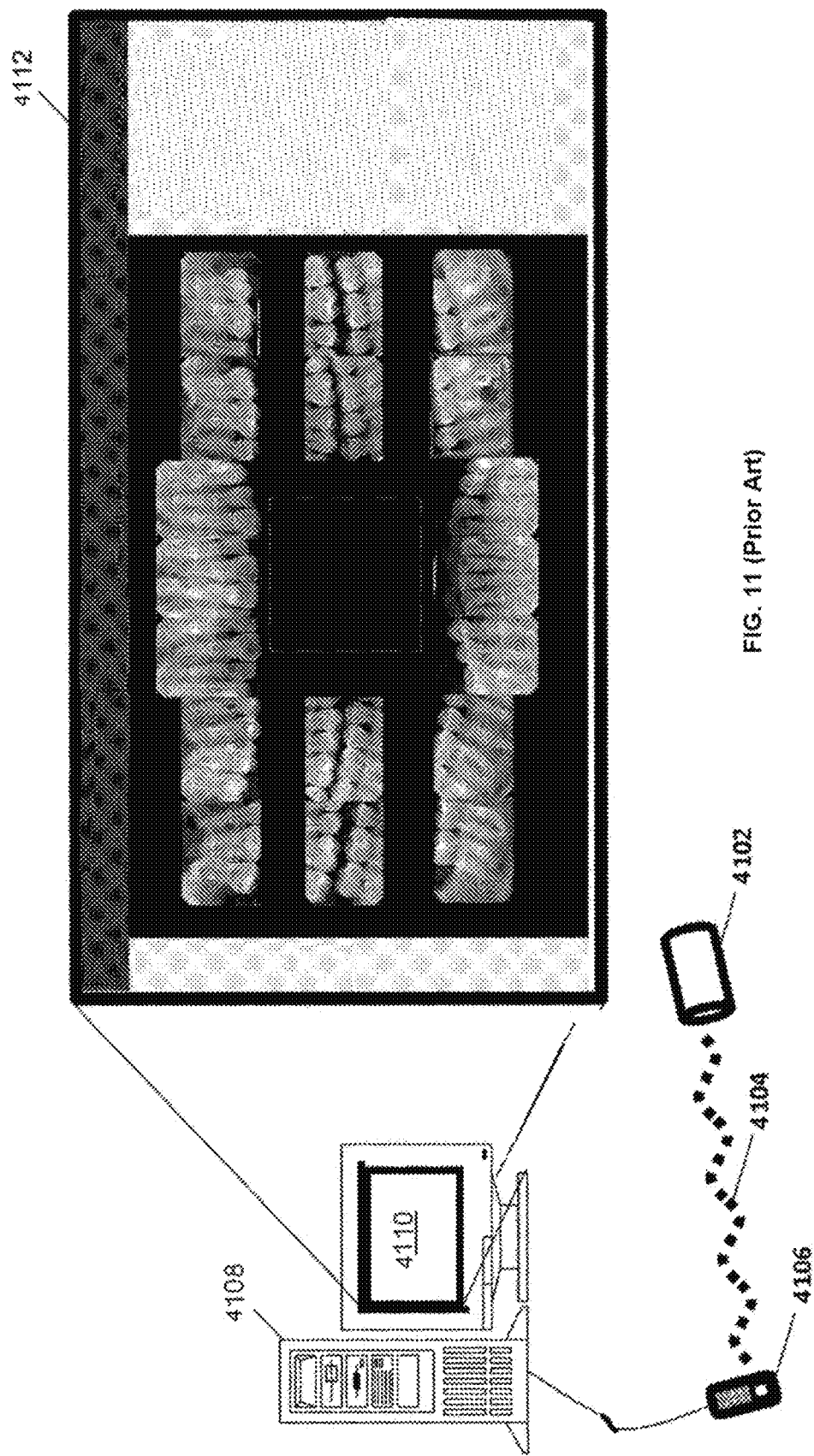
FIG. 11 is an illustration of a networking system according to U.S. Pat. No. 10,496,723.
Figure 12:
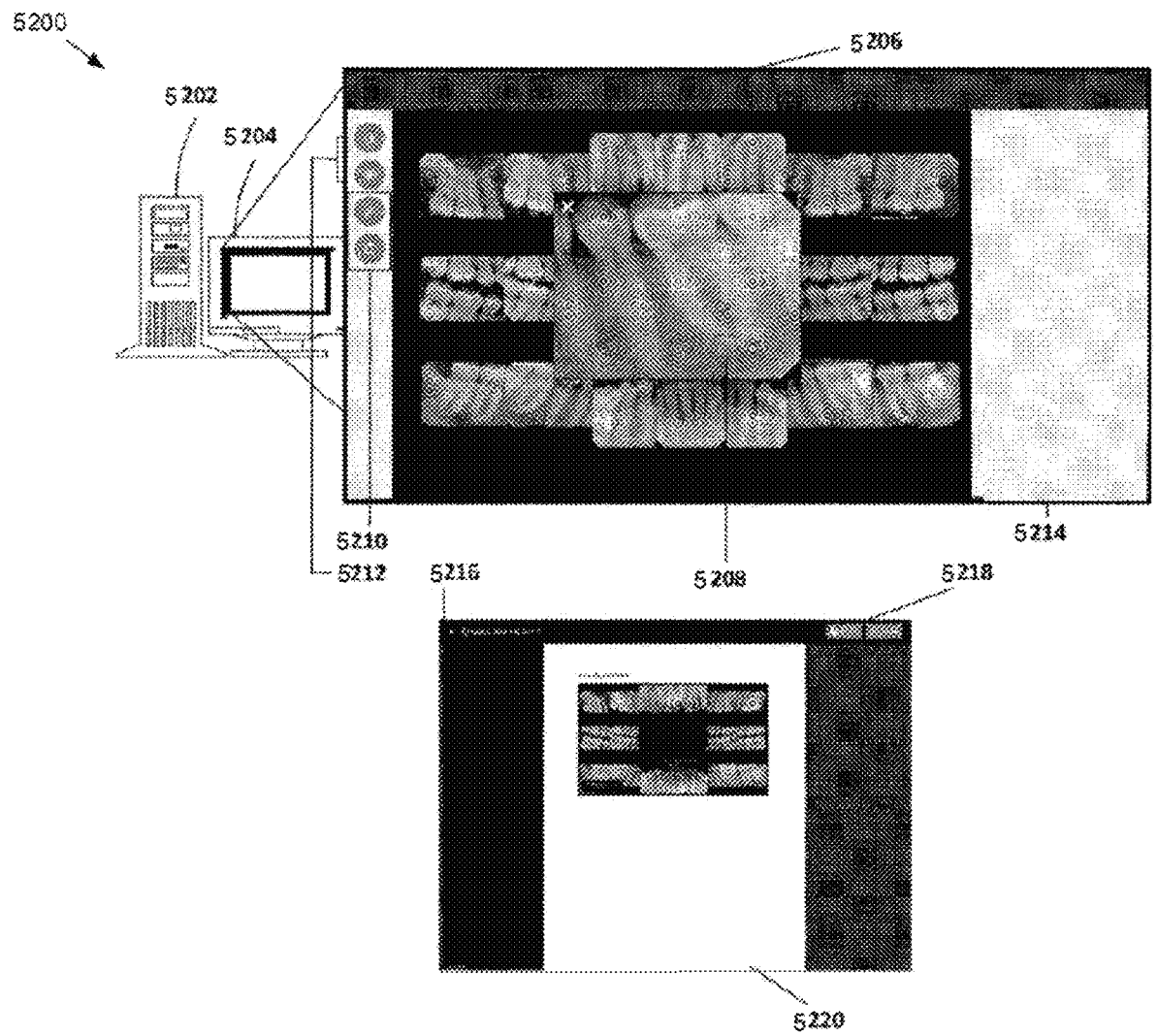
FIG. 12 is an illustration of a cloud-based server engine according to U.S. Pat. No. 10,496,723.
Figure 13:
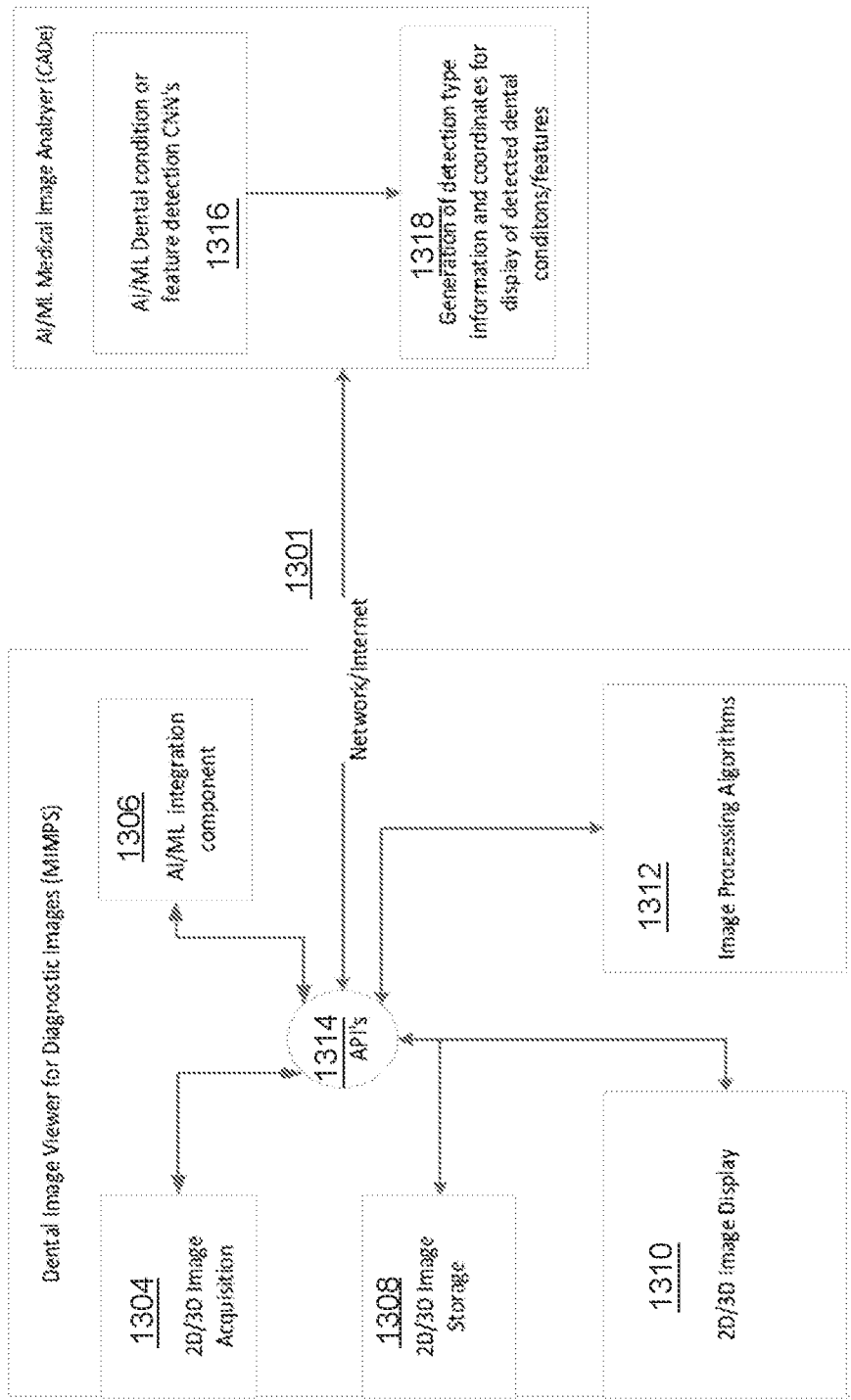
FIG. 13 is an illustration of a computing/network environment which includes a client-side dental image viewer (MIMPS device) that contains or is coupled to one or more AI/ML convolution neural networks via a network/internet connection and which convolution neural networks are trained for analyzing dental images (CADe device) according to the present invention.

Referring to FIG. 13, a computing environment for implementation of a process includes a MIMPS dental image viewer 1300 coupled to a CADe medical image analyzer 1302 via network/internet connection 1301. Dental image viewer 1300 consists of an acquisition component 1304 which implements ability to acquire images from dental imaging devices, a local or network storage component 1308 for storing acquired or imported images containing dental anatomy, a display component 1312 for displaying 2D or 3D dental anatomy images in a software user interface, image processing algorithms libraries 1312 implementing various standard and proprietary image processing routines, and an AI/ML integration component 1306 for coupling to and/or performing AI/ML analysis upon dental anatomy images. Medical image analyzer 1302 consists of one or more convolution neural networks 1316 for detecting a specific type of dental condition/feature and includes capabilities to generate coordinates for correlating display of the specific detected dental condition/feature 1318 via graphically annotating/overlaid upon the image which was analyzed by AI condition/feature detection component 1316. Dental image viewer 1300 implements various APIs to communicate information or data amongst the Dental Imaging Viewer sub-components 1304, 1306, 1308, 1310, 1312 and facilitates interfacing with Network/internet 1301. Dental image viewer 1300 integrates and couples to medical image analyzer 1302 via AI integration component 1306 and Network/internet connection 1301. Dental anatomy Images 1308 are communicated between the medical image analyzer 1302 and dental image viewer 1300 utilizing dental image viewer storage component 1308 and API's 1314 and which images are received by medical image analyzer 1302 and routed to AI/ML dental condition/feature detection CNN's 1316 for AI analysis.

Figure 14A:
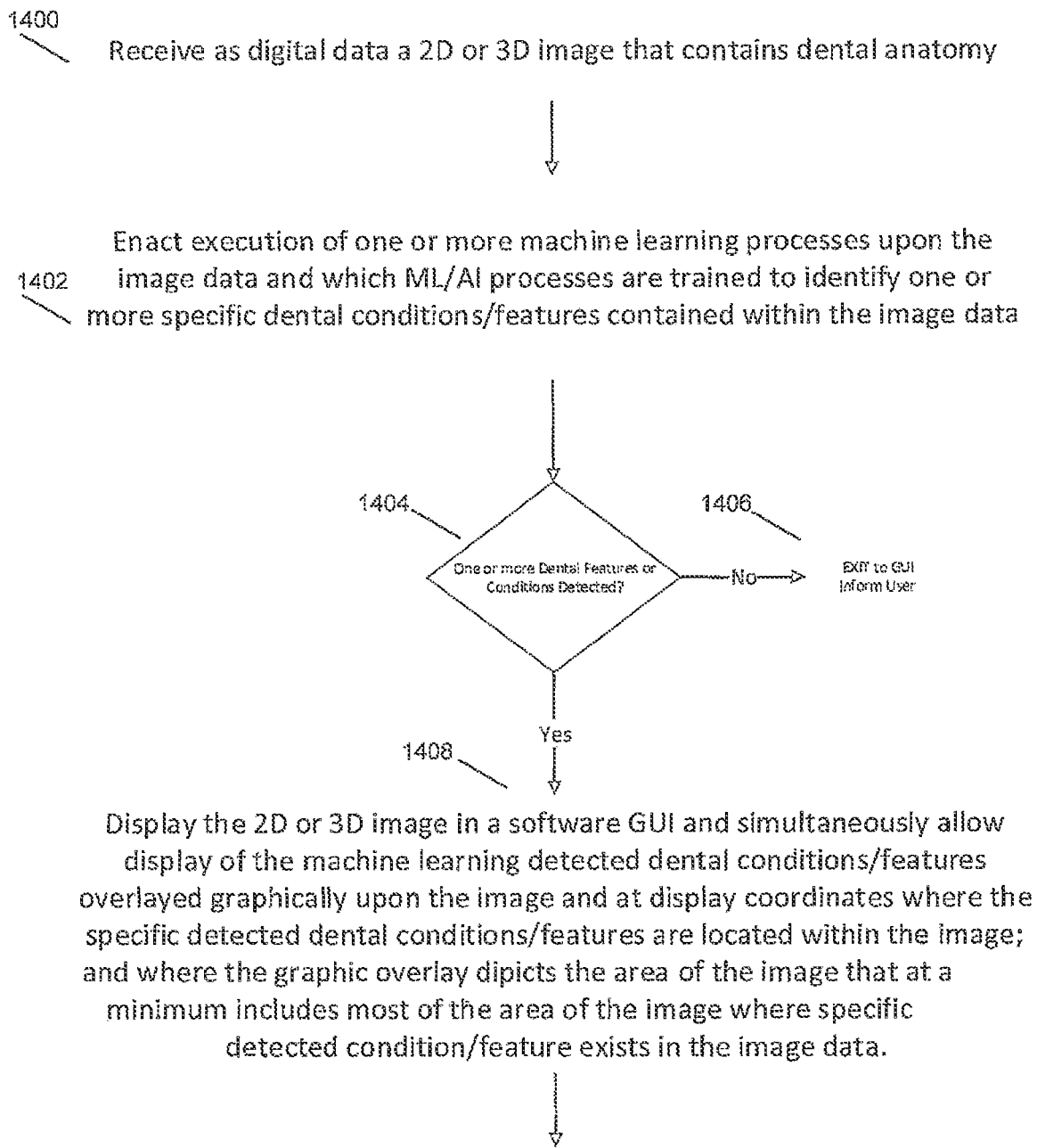
FIG. 14A is the first half of a flow chart that illustrates the data and process flow according to the present invention.
Figure 14B:
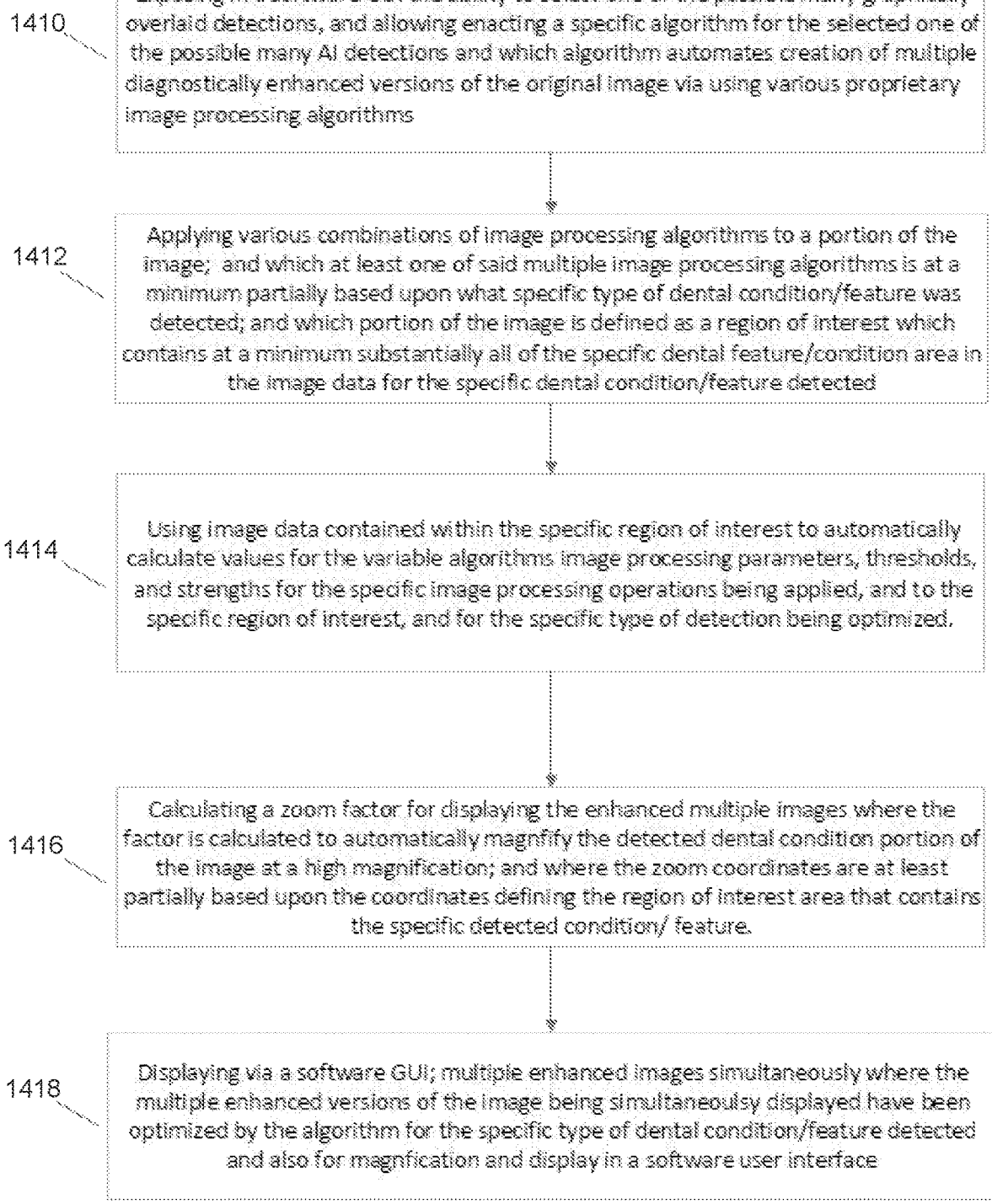
FIG. 14B is the second half of the flow chart that illustrates the data and process flow according to the present invention.

Referring to FIG. 14A and FIG. 14B, a flowchart shows data, process, and algorithm flow. The first flowchart entry 1400 which is a digital image file and is received contains pixel data representing dental anatomy/teeth. The ML/AI convolution neural networks that have been trained to identify specific dental anatomy conditions 1402 are enacted upon the digital image data to analyze for a specific dental condition/feature. The type of dental conditions/features that can be detected 1402 can include caries, periodontal pocket depth, open diastema, stained teeth, inflamed gingiva, apical lesions, erupted visible lesions, endo canals and lengths, root fractures, tooth tilt/angulation, veneers, supernumerary teeth, existing implants, existing crowns, existing fillings, leaky filling, tartar, TMJ, missing teeth, primary teeth, permanent teeth, chipped teeth, number of roots on tooth, tooth number/region, and tooth type including periapical, occlusal, and bitewing. When the AI/ML/CNN processes have completed 1402 next process flow 1404 is determined by whether at least one condition/feature was detected. If no dental conditions/features were detected in the digital image data, then the program flow exits the algorithms and informs user via a software GUI that no conditions/features were detected 1406. If at least one dental condition/feature was detected, then the process continues to 1408 display image and detection results graphically. The dental image (digital pixel data is displayed to the user in a software GUI and the detected condition/feature is identified upon the image and communicated to the user via a graphical means of overlaying a colors, lines, or graphics that signify/correlate the area of the image (region of interest that contains the detected dental condition/feature. After the image is displayed and the graphical means of annotating the detected condition/feature is displayed; the software GUI exposes means for users to select 1410 one of the possible many detected conditions/features that may be displayed/communicated graphically upon the image. The selection of a specific one of the many detections enables ability to enact the enhancement algorithm (either automated or via user interaction with GUI and which algorithm 1412 internal process flow is at least partially based upon the specific detected dental condition/feature type. The algorithm 1412 also defines a region of interest identifying a specific portion of the full image area/pixels where that defined region of interest contains pixel data for all the image area/pixels that contain the specific detected and selected one of many dental conditions/features; and which region of interest does not contain all the pixel image data for the full image. The algorithm processes image pixel data and image information 1414 using various combinations of proprietary and non-proprietary image enhancement techniques and where the techniques utilized are at least partially guided by the specific selected detection type; and at least partially based upon using a sub-set of the total image pixel data via using a region of interest that encompasses substantially all of the image pixel data area of the image where the specific detected and specific selected dental condition/feature exists. The methods of image processing applied may include pixel value min/max/average, distribution, histogram of pixel intensities, thresholding, segmentation of image to identify tooth structures, sub-segmentation that identifies dentin/enamel/tissue saliva/teeth spacing, color or grayscale pixel data, pixel size, average noise, min or average background level, region of interest pixel data compared to non-region of interest area pixels of the image, inversion of pixel data, non-liner LUT/remap pixel data, pseudo color mapping of pixel data, pseudo color mapping of detected structures of sub-segmentation, multi-scale sharpening, un-sharp masking, gaussian blur, multi-scale pixel smoothing, gamma, equalization, and window leveling. The methods of image processing implemented may also include digital subtraction or digital comparison methods for the specific region of interest detected and selected if the algorithm; which varies for the specific type of detection being processed; utilizes historical images as a portion of the automated diagnostic image enhancement and/or optimized diagnostic display processes. The digital comparison process includes obtaining one or more historical images for the patient that contain the same tooth anatomy as the image being analyzed and creates a correlating region of interest within the historical image of the detected condition area, and may also align the region of interest pixel data from the multiple regions of interest via sub-segmentation of the specific feature of that specific detected and selected condition/feature of the image being analyzed to historical image(s) to correlate. The digital comparison also can create information to graphically show the comparison results of the regions of interest areas and/or to graphically show data differences between the two or more regions of interest that have the detected condition/feature and visually showing pixel value differences, overlap or no overlap that exists within/between the two or more regions of interest used in the comparison. The algorithm implements automated image processing initial parameter value adjustment 1414 via using pixel data from the full image and the specific region of interest area where the variable values computed are at least partially based upon the specific pixel intensity values, pixel size, or subset of segmented pixels; that are contained substantially within the region of interest area for the specific AI detected and selected one of possible many dental conditions/features. The algorithm also implements automated calculation of display and magnification properties 1416 for the multiple created enhanced images which will be displayed simultaneously 1418 in a software GUI; typically, via a software medical image viewer or CADe software as shown in FIG. 13. The calculated an optimized magnification factor 1416 for use in displaying that specific detected dental condition/feature is based at least partially upon type of dental condition/feature detected and may also be based partially upon the pixel information or quantity of pixels defined in the region of interest that encompasses the detected and selected dental condition/feature. The multiple enhanced images are optimized for magnification for user viewing in a software GUI on a display monitor and for the specifically detected and selected one of many possible detections. The algorithm may also utilize the total number of enhanced images created for display as a portion of the method to calculate an image zoom factor for the images when displayed. The algorithm may also use viewing monitor dimensions or viewing pc display pixel resolution to set a portion of the optimized magnification factor. The display optimization algorithm may also rotate the image for optimized orientation of the detected condition and/or rotate the image or region of interest containing the detected and selected condition to optimize the number of enhanced and diagnostically optimized images that will be displayed in the software GUI to the user. The zoom factor may use a second region of interest in one or more of the enhanced images created; and which second region of interest encompasses the first region of interest portion of the full image that contains the detected dental condition/feature, and where the 2nd region of interest is utilized for displaying the specific detected and selected condition/feature highly magnified upon the viewing screen and which second region of interest was computed at least partially via pixels or pixel coordinates contained in the first region of interest and partially by the specific type of dental condition/feature detected.

Prior to display of the diagnostically enhanced images to the user, the system has received the image/image data 1400, enacted the AI CNN's 1402 upon the image data, displayed the detected dental conditions/features graphically overlaid upon the image in a software GUI 1408, the user or system enacted the enhancement algorithm for the one selected of possible many detections 1410, and the algorithm applies various proprietary imaging processing techniques to create enhanced diagnostic versions of the image 1412 containing the detected and selected dental condition, computes the image processing optimized values/parameters automatically for the enhanced images and regions of interest 1414, and calculated an optimized magnification factor 1416 for displaying that dental condition/feature and which magnification factor is based at least partially upon type of dental condition/feature detected, and may also be based upon the pixel information or quantity of pixels defined in the region of interest that encompasses the detected and selected dental condition/feature. The automatically created multiple enhanced and magnified images are displayed simultaneously in a software user interface 1418 allowing for visual diagnostic simultaneous comparison by the user of the multiple enhanced versions of images and regions of interest for that specifically detected dental condition/feature. The multiple enhanced images are displayed at a high magnification which was calculated based upon the region of interest and specific type of dental condition/feature detected. Users of the system can diagnostically compare the simultaneously displayed automatically created enhanced images and with high magnified region of interest displayed automatically, and where the enhanced images and display of the enhanced images simultaneously have been created for that specific type of AI detected dental condition/feature.

Referring again to FIG. 14A and FIG. 14B, the flowchart includes the steps of receiving as a digital 2D or 3D image that contains dental anatomy, enacting execution of one or more machine learning processes upon the image data which ML/AI processes are trained to identify one or more specific dental conditions/features contained, and if one or more dental features or conditions detected displaying the 2D or 3D image in a software GUI and simultaneously allowing display of the machine learning detected dental conditions/features overlayed graphically upon the image and at display coordinates where the specific detected dental conditions/features are located within the image. The graphic overlay encompasses an area of the image that at a minimum includes most of the area of the image where specific detected condition/feature exists in the image data. If neither a dental feature nor dental condition is detected, then exit to GUI and inform user.

Referring again to FIG. 14B the flowchart also includes the steps of exposing in a software GUI the ability to select one of the possible many graphically overlaid detections, and allowing enacting a specific algorithm for the selected one of the possible many AI detections and which algorithm automates creation of multiple diagnostically enhanced images using various combined proprietary image processing algorithms, applying various combinations of image processing algorithms to a portion of the image; and which at least one of said multiple image processing algorithms is at a minimum partially based upon what specific type of dental condition/feature was detected; and which portion of the image is defined as a region of interest which contains at a minimum substantially all of the specific dental feature/condition area in the image data for the specific dental condition/feature detected and using image data contained within the specific region of interest to automatically calculate values for the variable algorithms image processing parameters, thresholds, and strengths for the specific image processing operations being applied, and to the specific region of interest, and for the specific type of detection being optimized.

Still referring again to FIG. 14A and FIG. 14B, the flowchart further includes the steps of calculating a zoom factor for displaying the enhanced multiple images where the factor is calculated to automatically magnify the detected dental condition portion of the image at a high magnification; and where the zoom coordinates are at least partially based upon the coordinates defining the region of interest area that contains the specific detected condition/feature and displaying via a software GUI; multiple enhanced images simultaneously where the multiple enhanced versions of the image being simultaneously displayed have been optimized by the algorithm for the specific type of dental condition/feature detected and for magnification and display in a software user interface.

Figure 15A:
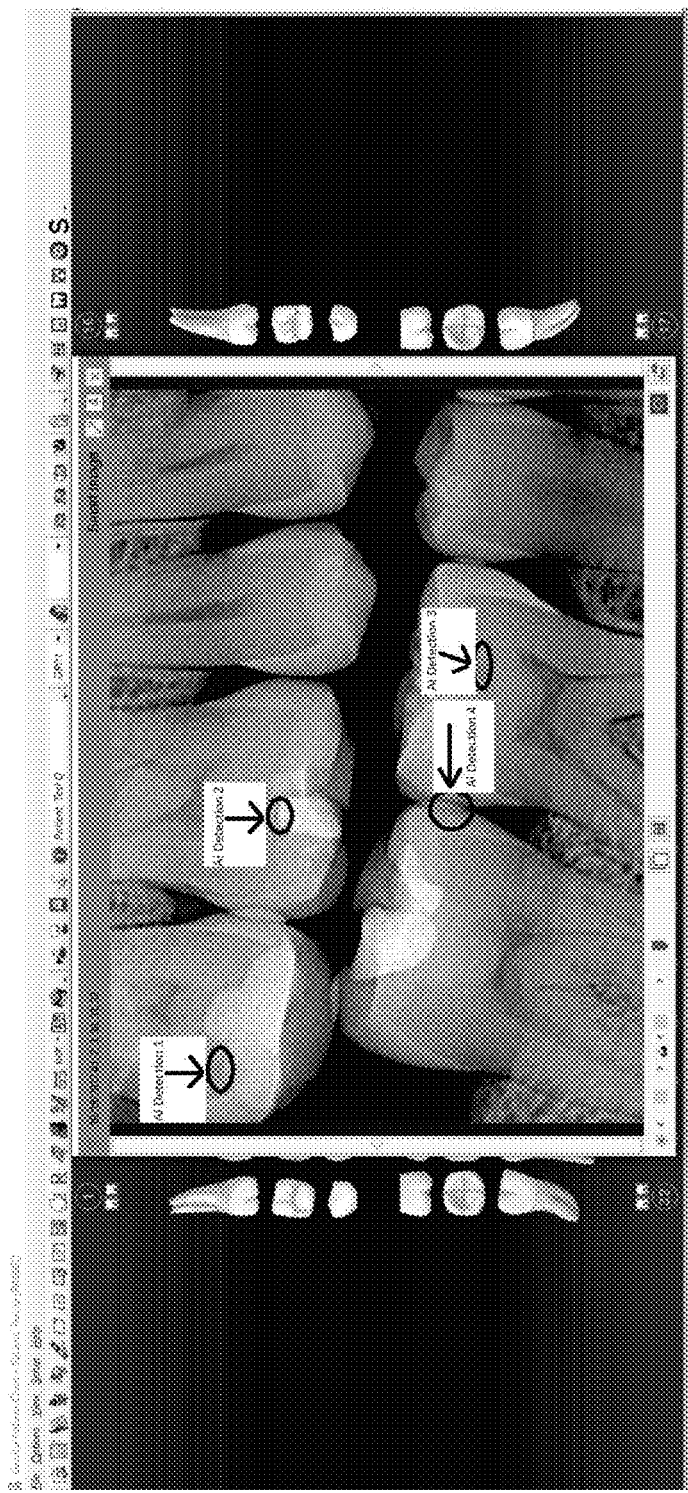
FIG. 15A is the first half of screen capture of the workflow according to the present invention.
Figure 15B:
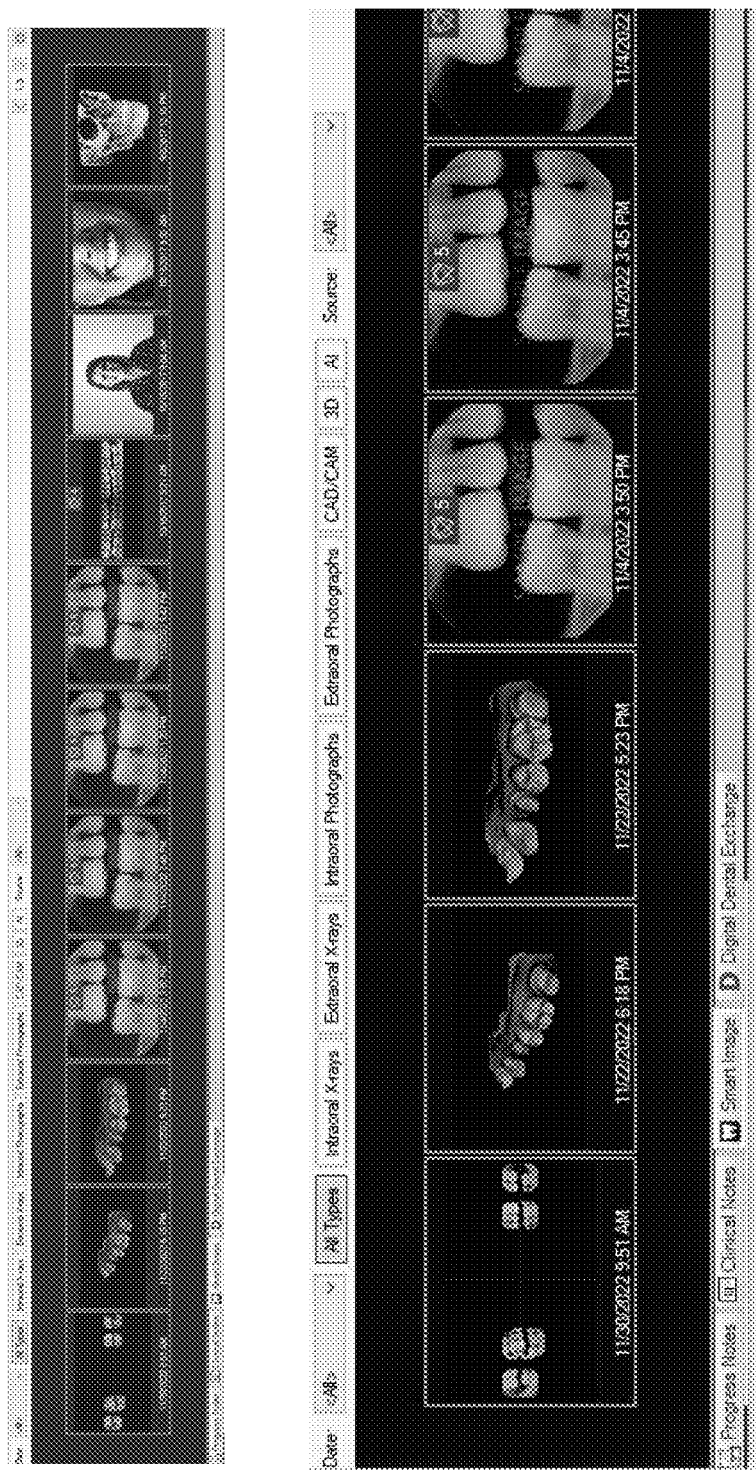
FIG. 15B is the second half of screen capture of the workflow according to the present invention.

Referring to FIG. 15A and FIG. 15B in conjunction with FIG. 13, FIG. 14A and FIG. 14B a screen capture 1500 of a MIMPS/dental image viewer software displays an image with dental anatomy (bitewing teeth and graphically overlaying rectangles utilizing bounding rectangles (four detected conditions/rectangles in this image that encompasses the dental condition detected (dental caries by AI/ML convolution neural networks having analyzed the image data contained within the image being displayed in the dental viewer. This equates to the system defined in FIG. 13 and step 1400 through step 1408 of FIG. 14A and FIG. 14B.

Figure 16A:
FIG. 16A is the first half of screen capture of the workflow according to the present invention.
Figure 16B:
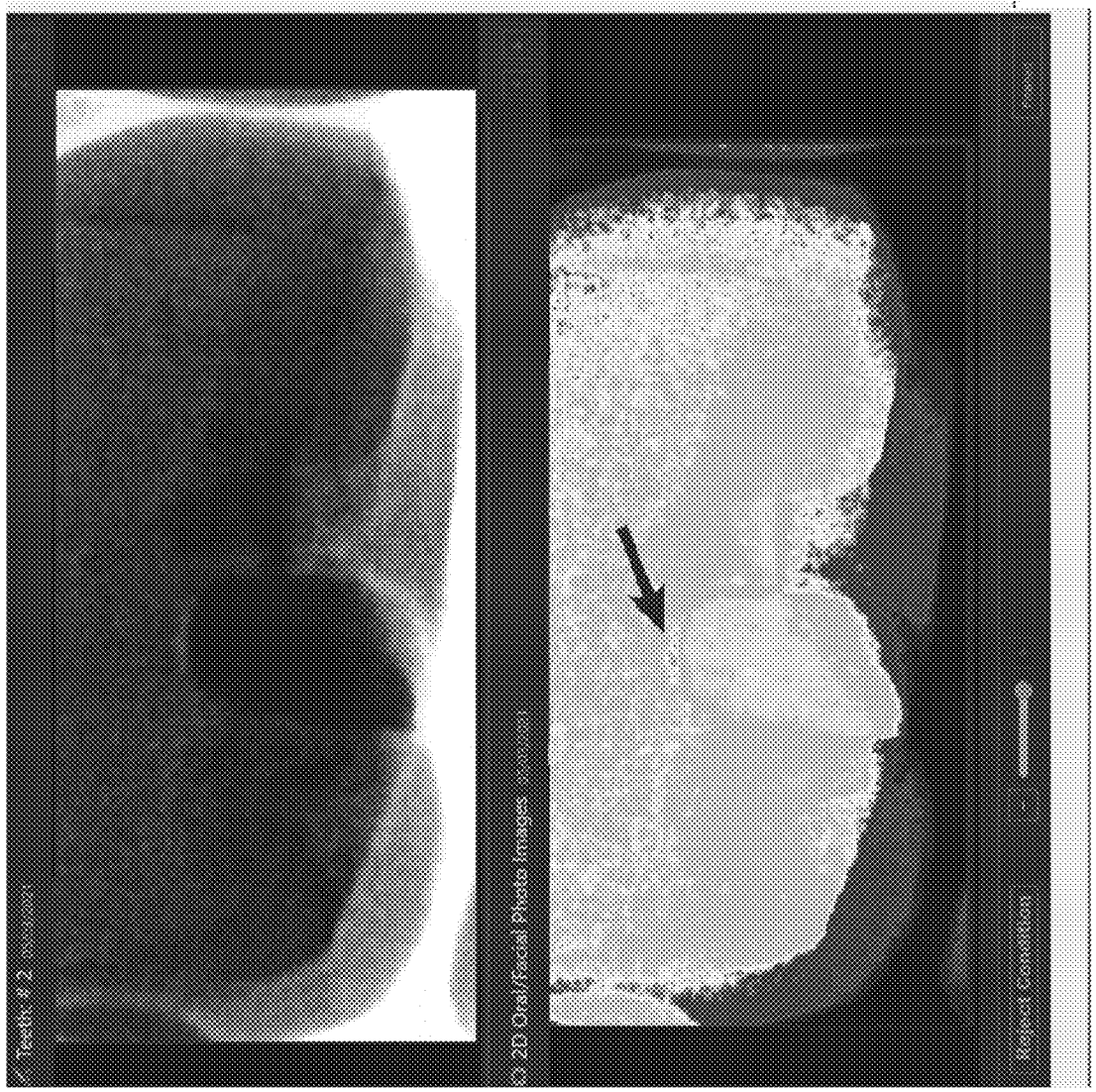
FIG. 16B is the second half of screen capture of the workflow according to the present invention.

Referring to FIG. 16A and FIG. 16B a screen 1600 capture of the MIMPS/dental image viewer software displays the results of the automatic enhancement and display algorithm for the specific user selected one AI detection of the possible many AI-detected conditions in the image. This equates to the system defined in FIG. 13 and step 1410 through step 1418 of FIG. 14A and FIG. 14B.

Referring to FIG. 15A and FIG. 15B in conjunction with FIG. 16A and FIG. 16B, a description of the workflow and algorithm processes and steps is described in the following additional information. For selecting the possible one of many AI detections present in the image (caries type of AI detections in the screencaps, the user may click a single GUI button, and which enacts the algorithm that creates multiple enhanced diagnostically accentuated images for the specific detected AI dental condition and displays these multiple images (sets upon the monitor/screen for simultaneous diagnostic review; and which the algorithm for this Caries also processed additional multiple historical images containing same anatomy and which are also used in the following example. The algorithm when enacted automatically created and displayed multiple windows (and which windows/images display enhanced/algorithmic proprietary image processed images and as a first displayed image the algorithm used multi-step image processing to create a look up table for the densities contained substantially within a specific region of interest that encompasses at a minimum substantially all of the AI detected condition that exists within a bounding region within the image that contains the AI detected condition. The algorithm creates and displays a second image which is a pseudo color mapped image that accentuates the region of interest densities via color mapping and by performing sub-segmentation upon the caries detected area portion of the image and which pixel data is used to generate the pseudo-color mapping range and color. The algorithm also creates and displays a third image which is an inverted pixel density image with level adjustments set by calculating adjustment level via the data in the region of interest portion of the image only (which contains the AI detected condition bounding box/rectangle and which increases contrast appropriately optimized specifically for that region of interest area (detected dental condition area only. The algorithm also creates a fourth image for display which is a composited image of the results of digital subtraction of multiple images that contain the same dental anatomy and which algorithm first aligns the anatomy of the AI detected condition region of interest of the first image to the equivalent region of interest area upon a 2nd or more images of the multiple images, and then second interprets via comparison or digital subtraction the pixel value differences in the region of interest aligned areas; and third display a composited image with the results of the interpretation/subtraction via using a semi-transparent color for each of the individual aligned image regions of interest from the multiple images and an additional color overlaid showing the non-overlapping or overlapping areas of the region of interest detected AI dental condition (caries area on the image from the multiple images used by the algorithm. The one bounding rectangle/detection is selected by the user via a GUI and the algorithm automatically creates multiple (three diagnostically enhanced versions of the image and displays the automatically created enhanced images region of interest at a high magnification for optimized viewing. The region of interest displayed within the enhanced image contains substantially all the area of the full image that contains the detected dental condition. In addition to the automatically created enhanced images, the original image is displayed showing the one of possible many detections overlaid upon the image via a graphical bounded box rectangle encompassing substantially all the detected dental condition/feature.

The first focus of the present invention is a computing device implemented method which includes the steps of sending one or more images of dental information which is a 2d or 3d image or image(s) containing dental anatomy to a convolution neural network-based machine learning (AI) software which has been trained to identify specific dental conditions or features, enacting of one or more machine learning convolution neural networks to detect a specific dental condition from a set of dental features or conditions and displaying one or more images with the detected dental condition(s) annotated graphically upon the image and in a location annotating the detected dental condition/feature. The computing device implemented method also includes the steps of exposing in the user interface the ability for a user to select one of the possible many AI detections that are detected and annotated graphically upon the image, in response to user input, enacting an algorithm for the selected one of the possible many ai detections whereby said algorithm automates creation of multiple enhanced images using various combined proprietary image processing algorithms and applying various combinations of image processing algorithms to at a minimum the portion of the image which is defined via a region of interest and where the region of interest contains substantially all the features or dental conditions detected for the selected one of possible many AI detections selected within the image or images. The computing device implemented method further includes the steps of displaying multiple images (sets of images) simultaneously in the user interface where the multiple images are enhanced versions of the image being displayed and are based upon the proprietary image processing algorithms and magnifying one or more the images (sets of images) being displayed and automatically adjusting the zoom factor upon display of the images to highly magnify the defined region of interest area that contains the graphically annotated selected one of possible many AI dental feature or condition detected. The algorithm displays the original non-enhanced image in the set of displayed images for the one of possible many selected detections and displays the original non-magnified image in the set of displayed images for the one of possible many selected detections. The algorithm varies image processing parameters, values, or function for the one of possibly many selected detections based upon the specific type of dental feature or condition detected and uses image data within the specific region of interest to automatically calculate values for optimizing variable algorithm parameters, thresholds, and strength of the image processing being applied to the specific region of interest and where the variable values set are at least partially based upon the specific pixel intensity value, pixel size, or area of the image containing the specific AI detected dental feature or dental condition. The set of dental conditions or features detected may include but is not limited to dental caries, endo canals identification, endo canal length, bone loss, periodontal pocket depth; existing crowns, existing fillings, existing mis-aligned teeth, existing implants, tartar, adult dentition, pedo dentition, overbite, underbite, and periodontal lesions. The algorithm uses multiple historical images of the patients same dental anatomy for analysis and wherein multiple historical images are segmented and aligned to the equivalent region of interest containing the detected condition or feature to display the annotated results graphically via a method of displaying the differences in pixel value or pixel density of detected feature or condition between the two or more images via using digital subtraction and comparison of the segmented and image data aligned images and uses multiple historical images of the patients same dental anatomy for analysis and wherein multiple historical images are segmented and aligned to the equivalent region of interest containing the detected condition or feature to display the annotated results graphically via a method of displaying the differences in size of the detected feature or condition between the two or more images via using digital subtraction and comparison of the segmented and image data aligned images.

The second focus of the present invention is upon automating diagnostic presentation of a machine learning/AI detected dental condition or dental feature to assist with diagnosis and/or feature identification. When dentists apply machine learning/AI in their practice one of the common issues that occurs is that the dentist does not have full confidence in the AI results (AI detected dental condition/feature). This is most often caused because the AI algorithm detected a condition; dental caries that is annotated upon the image by the AI software overlaying a label or bounding box as described above but the dentist cannot see the condition visually when the image is presented upon the computer monitor/display device. This is often caused because the AI algorithms are trained for the specific patterns which signify and detect that condition extremely well. Caries on dental teeth anatomy is detected extremely well by an AI CNN analyzing the image but not all caries conditions are easily seen via a human unaided eye. Some more technical dental users try to manually process/adjust the image using basic image enhancement tools. Even when some more complex image processing tools are available to the user most often users do not know the technical values and combinations of tools/image processing features to apply to an image for a specific imaging processing algorithm to accentuate that specific machine learning detected condition; and no dental imaging software is optimized for processing specific AI-detected condition within an image for a specific region of interest for specific dental conditions. In addition, because dentists do not typically have time during the patient appointment to try and adjust image processing and display related parameters for each detected condition and/or the specific data contained within that specific image for that dental condition, they often do not analyze sufficiently the AI detected condition to confirm if it is an actual dental pathology issue. This limits the real-world effectiveness and productivity of applying AI in the dental office via computer assisted detection devices (CADe).

The proposed invention solves the above issues by providing automated diagnostically enhanced creation and presentation of the AI detected dental condition in the image via an algorithm applied to the region of interest that includes at a minimum substantially all of the specific area in the image for the specific AI detected condition, and which algorithm applies conditional multi-step image processing to that specific region of interest area of the image for that specific AI detected dental condition and the algorithm creates multiple enhanced image sets for simultaneous presentation of the multiple enhanced images to the user that accentuate that specific type of detected dental condition for diagnosis or feature identification. The dental conditions or features that may be automatically optimized for identification/diagnosis by the invention may be one or more of the following including caries, periodontal pocket depth, inflamed gingiva, apical lesions, erupted visible lesions, endo canals, root fractures, implants, existing crowns, existing fillings, leaky filling, tartar, TMJ, missing teeth, primary teeth, permanent teeth, chipped teeth, number of roots on tooth, tooth number, and tooth type including periapical, occlusal, and bitewing. The dental condition specific multi-step algorithmic and automatic adjustment of the image processing applied to the detected (via AI) dental condition for automated enhancement of the image or region of interest may include multi-scale image processing, sharpness, gaussian blur, digital subtraction of multiple images containing the same AI detected dental condition, digital subtraction of multiple images not containing the same detected dental condition, digital subtraction of substantially only the segmented regions of interest, convolution kernels to the specific region(s) of interest, noise reduction, look up tables to remap density values within the region of interest only, contrast enhancement using data from the regions of interest only, histogram/levels processing using the entire image, images, or only substantially all of the region of interest area specific to a detected dental condition, density color mapping, minimum, mean, or maximum gray or color level density, equalization, inversion of grayscale or color pixel value, MIP/Raycast/VR or other rendering methods applied to substantially only the region of interest or multiple regions of interest. The algorithm that creates the multiple diagnostic presentation images may use metadata of the images or regions of interest and may use sub-segmentation within the AI detected condition image area in order to identify other dental related attributes including tissue, dentin, crown, root, DEJ, canal length, tooth position, tooth number, tooth area or dimensions that may be contained within that specific tooth/region of interest area of the image which has a dental condition detected via an AI CNN; and which region of interest has conditional and specifically targeted algorithmic image processing applied for that specific dental condition area; using at a minimum substantially all of the AI detected region of interest area; and applies individual non-linear contrast enhancement values to the multiple segmented areas within the region of interest detected; and then optionally combines the multiple enhanced sub-segmented portions of image to create a composited image for display to user for enhanced diagnosis and dental feature identification capability. The display parameters for presentation of the automatically created enhanced multiple image sets is also automatically adjusted by the algorithm when displaying the multiple diagnostic presentation image sets including calculating optimized magnification of the specific portion of the image/bounding box area that contains that AI detected dental condition. The algorithm additionally automatically adjusts image display parameters based upon the specific dental condition detected by the AI/machine learning and allows auto-magnification and which feature automatically zooms into an optimized region of interest encompassing substantially all of the AI detected condition bounding box area of the detected condition and then is displayed within one or more multiple diagnostic presentation images created by the algorithm, thereby presenting a set of multiple diagnostic images at a high magnification which are aligned to the AI detected condition and optimized for diagnostic viewing upon a monitor/viewing screen via a human dentist. The display parameters that may be adjusted automatically via the algorithm include magnification factor which can display the AI CNN detected feature or dental condition at an auto-calculated zoom level to accentuate diagnostic viewing ability for a human interpreting the small one of possible many AI-detected features or conditions area that exists within the entire image. Display of the detected dental condition and setting of magnification factor can be based at least partially upon the full image pixel resolution or pixel size, setting of magnification factor can based at least partially upon the percentage of the total image area that the AI-detected condition encompasses, the magnification can be based at least partially upon the specific detected condition/feature type, or magnification factor can also be based can be based at least partially upon the image orientation. The display parameter algorithm can also perform automatic alignment (rotation/de-skew) of multiple regions of interest for display that contain the same type of detected dental condition, the display algorithm can display and set magnification of the detected condition/feature results of a digital subtraction/comparison operation using color mapping to graphically show results where image1 region of interest1 that contains the AI-detected condition is color one; and image2 region of interest2 is color two; and the region of interest portions of the image for the detected conditions are overlaid upon image 1 or image 2 in semi-translucent differing colors, the display algorithm may use color mapping of digital subtraction or comparison results of multiple regions of interest; each region shown in a different translucent color and an additional color showing the non-overlapping or over-lapping portions of the multiple region of interests that exist within the two or more images, the display algorithm may use automatic alignment (segmentation/sub-segmentation/rotation/de-skew) of multiple regions of interest for aligning of the images/data results for visual display and where a first image region of interest has a detected dental condition via AI and a 2nd or more images that contains the same dental anatomy as first image but may not contain the same dental condition detected by AI are displayed.

From the foregoing a method for automatically making a diagnostic presentation of a machine learning/AI detected dental condition or dental feature to assist with diagnosis and/or feature identification has been described. It should be noted that the sketches are not drawn to scale and that distances between the figures are not to be considered significant.

Accordingly, it is intended that the foregoing disclosure and showing made in the drawing shall be considered only as an illustration of the principle of the present invention.

What is claimed is:

1. A computing device implemented method comprising the steps of:
   a. sending one or more images of dental information which is a 2d or 3d image or image(s) containing dental anatomy to a convolution neural network-based machine learning (AI) software which has been trained to identify specific dental conditions or features; and
   b. enacting of one or more machine learning convolution neural networks to detect a specific dental condition from a set of dental features or conditions;
   c. displaying one or more images with the detected dental condition(s) annotated graphically upon the image and in a location annotating the detected dental condition/feature; and
   d. exposing in the user interface the ability for a user to select one of the possible many AI detections that are detected and annotated graphically upon the image;
   e. in response to user input, enacting an algorithm for the selected one of the possible many ai detections whereby said algorithm automates creation of multiple enhanced images using various combined proprietary image processing algorithms;
   f. applying various combinations of image processing algorithms to at a minimum the portion of the image which is defined via a region of interest and where the region of interest contains substantially all the features or dental conditions detected for the selected one of possible many AI detections selected within the image or images;

g. displaying multiple images (sets of images) simultaneously in the user interface where the multiple images are enhanced versions of the image being displayed and are based upon the proprietary image processing algorithms; and h. magnifying one or more the images (sets of images) being displayed and automatically adjusting the zoom factor upon display of the images to highly magnify the defined region of interest area that contains the graphically annotated selected one of possible many AI dental feature or condition detected.

2. A computing device implemented method according to claim 1 wherein said algorithm also displays the original non-enhanced image in the set of displayed images for one of many possible selected detections.

3. A computing device implemented method according to claim 1 wherein said algorithm also displays the original non-magnified image in the set of displayed images for the one of many possible selected detections.

4. A computing device implemented method according to claim 1 wherein said algorithm varies image processing parameters, values, or function for the one of many selected detections based upon the specific type of dental feature or condition detected.

5. A computing device implemented method according to claim 1 wherein said algorithm uses image data within the specific region of interest to automatically calculate values for optimizing variable algorithm parameters, thresholds, and strength of the image processing being applied to the specific region of interest and where the variable values set are at least partially based upon the specific pixel intensity value, pixel size, or area of the image containing the specific AI detected dental feature or dental condition.

6. A computing device implemented method according to claim 1 wherein the set of dental conditions or features detected may include but is not limited to dental caries, endo canals identification, endo canal length, bone loss, periodontal pocket depth; existing crowns, existing fillings, existing mis-aligned teeth, existing implants, tartar, adult dentition, pedo dentition, overbite, underbite, and periodontal lesions.

7. A computing device implemented method according to claim 1 wherein said algorithm uses multiple historical images of the patients same dental anatomy for analysis and wherein multiple historical images are segmented and aligned to the equivalent region of interest containing the detected condition or feature to display the annotated results graphically via a method of displaying the differences in pixel value or pixel density of detected feature or condition between the two or more images via using digital subtraction and comparison of the segmented and image data aligned images.

8. A computing device implemented method according to claim 1 wherein said algorithm uses multiple historical images of the patients same dental anatomy for analysis and wherein multiple historical images are segmented and aligned to the equivalent region of interest containing the detected condition or feature to display the annotated results graphically via a method of displaying the differences in size of the detected feature or condition between the two or more images via using digital subtraction and comparison of the segmented and image data aligned images.

* * * * *